United States Patent [19]
Zwaagstra et al.

[11] Patent Number: 6,136,848
[45] Date of Patent: Oct. 24, 2000

[54] FLAVONE DERIVATIVE AND MEDICINE COMPRISING THE SAME

[75] Inventors: Maria Elizabeth Zwaagstra, Amsterdam, Netherlands; Mingqiang Zhang, Lanarkshire, United Kingdom; Henk Timmerman, Voorschoten, Netherlands; Masahiro Tamura, Higashimurayama; Yasushi Wada, Tachikawa, both of Japan

[73] Assignee: Kowa Co., Ltd., Nagoya, Japan

[21] Appl. No.: 08/942,498

[22] Filed: Oct. 2, 1997

[30] Foreign Application Priority Data

Oct. 4, 1996 [JP] Japan ................... 8-264379

[51] Int. Cl.[7] .................. A61K 31/35; A61K 31/495; C07D 311/04
[52] U.S. Cl. .................. 514/456; 514/248; 514/255; 514/314; 514/367; 514/397; 549/403; 548/305; 548/159; 544/283; 544/364; 546/174
[58] Field of Search ................... 549/403; 514/456, 514/248, 255, 314, 367, 397; 548/305.1, 159; 546/174; 544/283, 364

[56] References Cited

U.S. PATENT DOCUMENTS

| | | | |
|---|---|---|---|
| 3,993,669 | 11/1976 | Pfister | 260/345.2 |
| 4,157,334 | 6/1979 | Doria e al. | 260/345.2 |
| 4,525,356 | 6/1985 | Itho et al. | 514/234 |
| 5,474,994 | 12/1995 | Leonardi et al. | 514/218 |

FOREIGN PATENT DOCUMENTS

| | | |
|---|---|---|
| 0 142 303 | 5/1985 | European Pat. Off. . |
| 24 61 670 | 7/1975 | Germany . |
| WO 94/01408 | 1/1994 | WIPO . |

OTHER PUBLICATIONS

Maria E. Zwaagdtra, et al., European Journal of Medicinal Chemistry, vol. 31, No. 11, pp. 861–874, "Synthesis of Carboxylated Flavonoids As New Leads for LTD4 Antagonists", 1996.
Chemical Abstracts, vol. 89, No. 13, AN 108943m, Sep. 25, 1978, p. 866.
Chemical Abstracts, vol. 92, No. 15, AN 121572w, Apr. 14, 1980, p. 22.
Chemical Abstracts, vol. 77, No. 3, AN 019485y, Jul. 17, 1972, p. 496.
Chemical Abstracts, vol. 87, No. 3, AN 022971r, Jul. 18, 1977, p. 623.
Chemical Abstracts, vol. 90, No. 19, AN 145560a, May 7, 1979, pp. 17–18.
Chemical Abstracts, vol. 119, No. 21, AN 225723p, Nov. 22, 1993, p. 989.
Chemical Abstracts, vol. 113, No. 17, AN 152089a, Oct. 22, 1990, p. 746.
Derwent Abstracts, AN 85–027860, JP 59 22 486, Dec. 14, 1984, 2 pages.
Chemical Abstracts, vol. 119, No. 17, AN 173825b, Oct. 25, 1993, pp. 48–49.

*Primary Examiner*—Amelia Owens
*Attorney, Agent, or Firm*—Oblon, Spivak, McClelland, Maier & Neustadt, P.C.

[57] ABSTRACT

This invention relates to a flavone derivative represented by the formula (1) or a salt thereof, and also to a medicine containing the same.

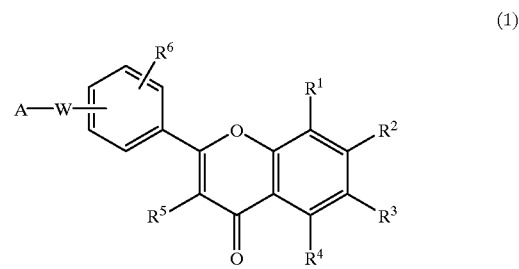

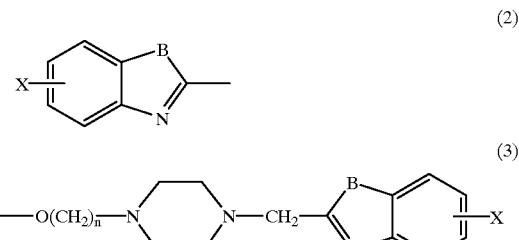

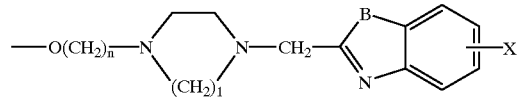

wherein A represents H, halogen, phenyl, naphthyl, a group of the formula (2) in which X is H or halogen, B is —CH=CH—, —CH=N—, —N($R^7$)— ($R^7$: lower alkyl or alkoxyalkyl), —O— or —S—; W represents a single bond, —$CH_2$O— or —CH=CH—; at least one of $R^1$ to $R^4$ represents —COOH, —CN, alkyloxycarbonyl, tetrazolyl or —CONH$R^8$ ($R^8$: H, lower alkyl or phenylsulfonyl), the remainder thereof individually represent H, halogen, —OH, lower alkyl or lower alkoxyl; $R^5$ represents H, —OH, lower alkoxyl, —O($CH_2$)$_m$N$R^9R^{10}$ ($R^9,R^{10}$: H or lower alkyl, or coupled together with the adjacent N to form a phthalimido group; m: 1–5), or a group of the formula (3) (n: 1–5, l: 2–3; and $R^6$ represents H, halogen, lower alkyl or lower alkoxyl. A situation where A is H or halogen, W is a single bond and $R^5$ is H is excluded. The compound (1) has excellent cys-$LT_1$ receptor antagonism.

11 Claims, No Drawings

FLAVONE DERIVATIVE AND MEDICINE COMPRISING THE SAME

BACKGROUND OF THE INVENTION a) Field of the Invention

This invention relates to a flavone derivative or a salt thereof, which is useful as a medicine.

b) Description of the Related Art

Peptidoleucotrienes $LTC_4$, $LTD_4$ and $LTE_4$, a group of metabolites of arachidonic acid, are known to act as important causal substances for bronchial asthma both in vitro and in vivo (Henderson, W. R., Jr. Ann. Intern. Med., 121, 684–697, 1994). As morbid conditions caused by leucotriene, there are airway constriction, mucosal oversecretion and pulmonary edema. They eventually induce an airway disorder which is a characteristic of asthma. Effects of $LTC_4$ or $LTD_4$ on airway constriction when inhaled reach 1,000 times as much as those of histamine. $LTE_4$ has lower activities compared with the other leucotrienes, but airway constriction induced by $LTE_4$ is long lasting compared with that caused by the other leucotrienes (Larsen, J. S., Acosta, E. P. Ann. Pharmacother, 27, 898–903, 1993).

Further, leucotrienes are stated to take part not only in asthma but also in various allergic diseases, autoimmune diseases, inflammatory diseases, cerebral ischemia, cerebral apoplexy and the like.

Keeping in step with discovery of roles of leucotrienes in biosynthesis pathways and diseases as mentioned above, there are increasing activities for the development of synthesis inhibitors for leucotriene, antagonists for $cys\text{-}LT_1$ receptor and the like with a view to reducing leucotrienes (Metters, K. M. J. Lipid Mediators Cell Signalling, 12, 413–427, 1995). According to some recent findings in clinical aspects, it has been indicated that $cys\text{-}LT_1$ receptor antagonists are extremely effective for various types of asthma (Taylor, I. K. Thorax, 50, 1005–1010, 1995; Pauwels, R. A., Joos, G. F. J. C. Allergy 30, 615–622, 1995). It is however the current situation that no compound has been found to be fully satisfactory in controlling action of leucotrienes.

SUMMARY OF THE INVENTION

An object of the present invention is therefore to provide a novel $cys\text{-}LT_1$ receptor antagonist having high inhibitory activities.

With the foregoing circumstances in view, the present inventors have proceeded with extensive research in attempts to obtain a novel $cys\text{-}LT_1$ receptor antagonist having high inhibitory activities. As a result, a compound represented by the below-described formula (1) has been found to be useful as a preventive or therapeutic for various diseases typified by allergic diseases because it has $cys\text{-}LT_1$ receptor antagonism and strongly inhibits action of leucotrienes, leading to the completion of the present invention.

The present invention therefore provides a flavone derivative represented by the following formula (1):

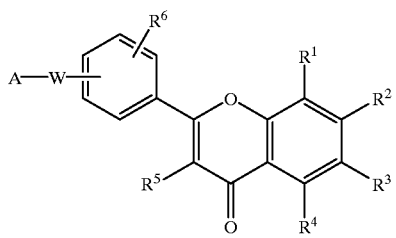

wherein A represents a hydrogen atom, a halogen atom, a substituted or unsubstituted phenyl group, a substituted or unsubstituted naphthyl group, or a group represented by the following formula (2):

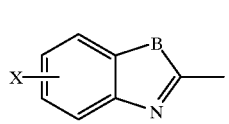

wherein X represents a hydrogen atom or a halogen atom, and B represents —CH=CH—, —CH—N—, —N($R^7$)— in which $R^7$ defined above, and $R^6$ represents a hydrogen atom, a halogen atom, a lower alkyl group or a lower alkoxyl group, with the proviso that a situation where A is a hydrogen atom or a halogen atom, W is a single bond and $R^5$ is a hydrogen atom is excluded; or a salt of the flavone derivative.

The flavone derivative or its salt will hereinafter be called the compound (1).

This invention also provides a medicine comprising as an effective ingredient the above-described compound (1).

Further, this invention also provides a medicinal composition comprising the above-described compound (1) and a pharmacologically acceptable carrier.

In addition, this invention also provides use of the above-described compound (1) in a medicine.

Furthermore, the present invention also provides a treatment method of an allergic diseases, which comprises administering an effective amount of the above-described compound (1).

DETAILED DESCRIPTION OF THE INVENTION AND PREFERRED EMBODIMENTS

In the compound (1) represented by the above for- represents a lower alkyl group or an alkoxyalkyl group, —O— or —S—, W represents a single bond, —$CH_2O$— or —CH=CH—, at least one of $R^1$, $R^2$, $R^3$ and $R^4$ represents a carboxyl group, a cyano group, a substituted or unsubstituted alkyloxycarbonyl group, a tetrazolyl group, or —$CONHR^8$ in which $R^8$ represents a hydrogen atom, a lower alkyl group or a phenylsulfonyl group, and the remainder thereof may be the same or different and individually represent a hydrogen atom, a halogen atom, a hydroxyl group, a lower alkyl group or a lower alkoxyl group, $R^5$ represents a hydrogen atom, a hydroxyl group, a substituted or unsubstituted lower alkoxyl group, —O($CH_2$)

$_mNR^9R^{10}$ in which $R^9$ and $R^{10}$ may be the same or different and individually represent a hydrogen atom or a lower alkyl group or are coupled together with the adjacent nitrogen atom to form a phthalimido group, and m stands for a number of 1–5, or a group represented by the following formula (3):

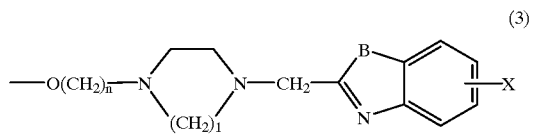

wherein n stands for a number of 1–5, l stands for a number of 2–3, and B and X have the same meanings as mula, illustrative of the halogen atom are fluorine, chlorine, bromine and iodine atoms. Illustrative of the lower alkyl group are linear or branched alkyl groups having 1–6 carbon atoms. Preferred examples of the alkyl group include methyl, ethyl, n-propyl, isopropyl, n-butyl, isobutyl, t-butyl, pentyl and n-hexyl, with methyl, ethyl and t-butyl being particularly preferred. Illustrative of the lower alkoxyl group are linear or branched alkoxyl groups having 1–6 carbon atoms, for example, methoxy, ethoxy, propoxy, butoxy and the like, among which methoxy is particularly preferred. Examples of the alkoxyalkyl group include $C_{1-6}$ alkoxy $C_{1-6}$ alkyl groups, for example, methoxymethyl, methoxyethyl, methoxypropyl, methoxybutyl, ethoxymethyl, ethoxyethyl, ethoxypropyl, ethoxybutyl, propoxymethyl, propoxyethyl, propoxypropyl, propoxybutyl and the like, with ethoxyethyl being particularly preferred. Further, Illustrative of the alkyloxycarbonyl group are $C_{1-6}$ alkyloxycarbonyl groups, for example, methyloxycarbonyl, ethyloxycarbonyl, propyloxycarbonyl, butyloxycarbonyl and the like, with ethyloxycarbonyl being particularly preferred.

Preferred examples of the substituted or unsubstituted phenyl group or the substituted or unsubstituted naphthyl group represented by A in the for- atoms.

At least one of $R^1$, $R^2$, $R^3$ and $R^4$ represents a carboxyl group, a cyano group, a substituted or unsubstituted alkyloxycarbonyl group, a tetrazolyl group, or —CONHR$^8$, and the remainder thereof may be the same or different and individually represent a hydrogen atom, a halogen atom, a hydroxyl group, a lower alkyl group or a lower alkoxyl group. A preferred situation is that one of $R^1$, $R^2$, $R^3$ and $R^4$ represents a carboxyl group, a cyano group, a $C_{1-6}$ alkyloxycarbonyl group, a tetrazolyl group or —CONHR$^8$ and the remainder thereof may be the same or different and individually represent a hydrogen atom, a halogen atom, a hydroxyl group, a lower alkyl group or a lower alkoxyl group.

In the compound (1) of the present invention, a preferred situation is that in the formula (1), A represents a substituted or unsubstituted phenyl group, a substituted or unsubstituted naphthyl group, or a group represented by the following formula (2):

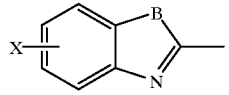

wherein X represents a hydrogen atom or a halogen atom, and B represents —CH=CH—, —CH—N—, —N(R$^7$)— in which R$^7$ mula (1) include a phenyl group which may be substituted by one or more halogen atoms, lower alkyl groups or lower alkoxyl groups; and a naphthyl group which may be substituted by one or more halogen atoms, lower alkyl groups or lower alkoxyl groups. More preferred are a phenyl group which may be substituted by one or more halogen atoms, $C_{1-6}$ alkyl groups or $C_{1-6}$ alkoxyl groups and a naphthyl group which may be substituted by one or more halogen atoms, $C_{1-6}$ alkyl groups or $C_{1-6}$ alkoxyl groups. Particularly preferred are phenyl and naphthyl.

Further, examples of the substituted or unsubstituted alkyloxycarbonyl group include $C_{1-6}$ alkyloxycarbonyl groups which may be substituted at alkyl moieties thereof by one or more halogen atoms, lower alkoxyl groups, substituted or unsubstituted phenyl group or phthalimido groups, with $C_{1-6}$ alkyloxycarbonyl groups being particularly preferred. Illustrative of the substituted or unsubstituted lower alkoxyl group are lower alkoxyl groups which may be substituted by one or more amino groups, alkylamino groups, dialkylamino groups or halogen atoms. Of these, preferred are $C_{1-6}$ alkoxyl groups which may be substituted by one or more amino groups, $C_{1-6}$ alkylamino groups, di-$C_{1-6}$ alkylamino groups or halogen represents a lower alkyl group or an alkoxyalkyl group, —O— or —S—, W represents —CH$_2$O— or —CH=CH—, at least one of $R^1$, $R^2$, $R^3$ and $R^4$ represents a carboxyl group, a cyano group, a substituted or unsubstituted alkyloxycarbonyl group, a tetrazolyl group, or —CONHR$^8$ in which R$^8$ represents a hydrogen atom, a lower alkyl group or a phenylsulfonyl group, and the remainder thereof may be the same or different and individually represent a hydrogen atom, a halogen atom, a hydroxyl group, a lower alkyl group or a lower alkoxyl group, $R^5$ represents a hydrogen atom, a hydroxyl group, a substituted or unsubstituted lower alkoxyl group, —O(CH$_2$)$_m$NR$^9$R$^{10}$ in which R$^9$ and R$^{10}$ may be the same or different and individually represent a hydrogen atom or a lower alkyl group or are coupled together with the adjacent nitrogen atom to form a phthalimido group, and m stands for a number of 1–5, or a group represented by the following formula (3):

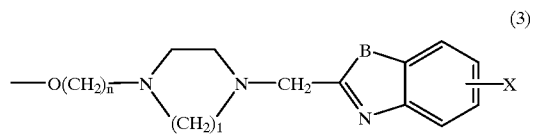

wherein n stands for a number of 1–5, l stands for a number of 2–3, and B and X have the same meanings as defined above, and $R^6$ represents a hydrogen atom, a halogen atom, a lower alkyl group or a lower alkoxyl group.

In the compound (1) of the present invention, another preferred situation is that in the formula (1), A represents a hydrogen atom or a halogen atom, W represents a single bond, at least one of $R^1$, $R^2$, $R^3$ and $R^4$ represents a carboxyl group, a cyano group, a substituted or unsubstituted alkyloxycarbonyl group, a tetrazolyl group, or —$CONHR^8$ in which $R^8$ represents a hydrogen atom, a lower alkyl group or a phenylsulfonyl group, and the remainder thereof may be the same or different and individually represent a hydrogen atom, a halogen atom, a hydroxyl group, a lower alkyl group or a lower alkoxyl group, $R^5$ represents a hydroxyl group, a substituted or unsubstituted lower alkoxyl group, —$O(CH_2)_m NR^9 R^{10}$ in which $R^9$ and $R^{10}$ may be the same or different and individually represent a hydrogen atom or a lower alkyl group or are coupled together with the adjacent nitrogen atom to form a phthalimido group, and m stands for a number of 1–5, or a group represented by the following formula (3):

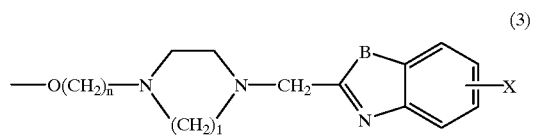

(3)

wherein n stands for a number of 1–5, l stands for a number of 2–3, and B and X have the same meanings as defined above, and $R^6$ represents a hydrogen atom, a halogen atom, a lower alkyl group or a lower alkoxyl group.

In the compound (1) of the present invention, a more preferred situation is that in the formula (1), A represents a substituted or unsubstituted phenyl group, a substituted or unsubstituted naphthyl group, or a group represented by the following formula (2):

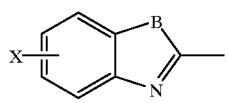

(2)

wherein X represents a hydrogen atom or a halogen atom, and B represents —CH=CH—, —CH—N—, —N($R^7$)— in which $R^7$ represents a lower alkyl group or an alkoxyalkyl group, —O— or —S—, W represents —$CH_2O$— or —CH=CH—, at least one of $R^1$, $R^2$, $R^3$ and $R^4$ represents a carboxyl group, a cyano group, a substituted or unsubstituted alkyloxycarbonyl group, a tetrazolyl group, or —$CONHR^8$ in which $R^8$ represents a hydrogen atom, a lower alkyl group or a phenylsulfonyl group, and the remainder thereof may be the same or different and individually represent a hydrogen atom, a halogen atom, a hydroxyl group, a lower alkyl group or a lower alkoxyl group, $R^5$ represents a hydrogen atom, a hydroxyl group, a substituted or unsubstituted lower alkoxyl group, or —$O(CH_2)_m NR^9 R^{10}$ in which $R^9$ and $R^{10}$ may be the same or different and individually represent a hydrogen atom or a lower alkyl group or are coupled together with the adjacent nitrogen atom to form a phthalimido group, and m stands for a number of 1–5, and $R^6$ represents a hydrogen atom, a halogen atom, a lower alkyl group or a lower alkoxyl group.

No particular limitation is imposed on the salt of the compound (1) of the present invention, insofar as it is a pharmacologically acceptable salt. Illustrative are metal salts such as the sodium salt, potassium salt, calcium salt, magnesium salt, manganese salt, iron salt and aluminum salt; mineral acid addition salts such as the hydrochloride, hydrobromide, hydroiodide, sulfate and phosphate; and organic acid addition salts such as the benzoate, methanesulfonate, ethanesulfonate, benzenesulfonate, p-toluenesulfonate, oxalate, maleate, fumarate, tartrate and citrate.

The compound (1) of the present invention may also exist in the form of solvates represented by the hydrate. Such solvates should also be included in the present invention. Further, the compound (1) of the present invention may also present in the form of a keto-enol tautomer. Such a tautomer should also be embraced in the present invention.

Among compounds (1) according to the present invention, compounds (1a) in which W is —$CH_2O$— can each be prepared by the following process.

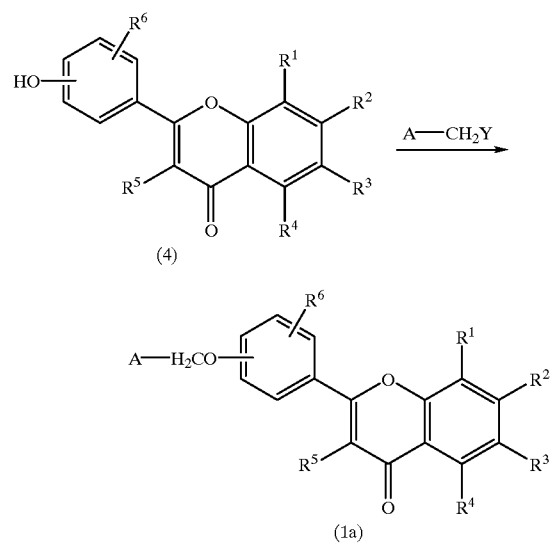

wherein A, $R^1$, $R^2$, $R^3$, $R^4$, $R^5$, and $R^6$ have the same meanings as defined above, and Y represents a chlorine atom, a bromine atom or an iodine atom.

Specifically, the compound (1a) of the present invention can be obtained by reacting a phenol compound (4) and a halomethyl compound, for example, in a solvent such as acetone or DMF (N,N-dimethylformamide) in the presence of a base such as potassium carbonate.

A hydroxyflavone compound (4a) of the formula (4) in which $R^5$ is H can be prepared by the following two synthesis processes.

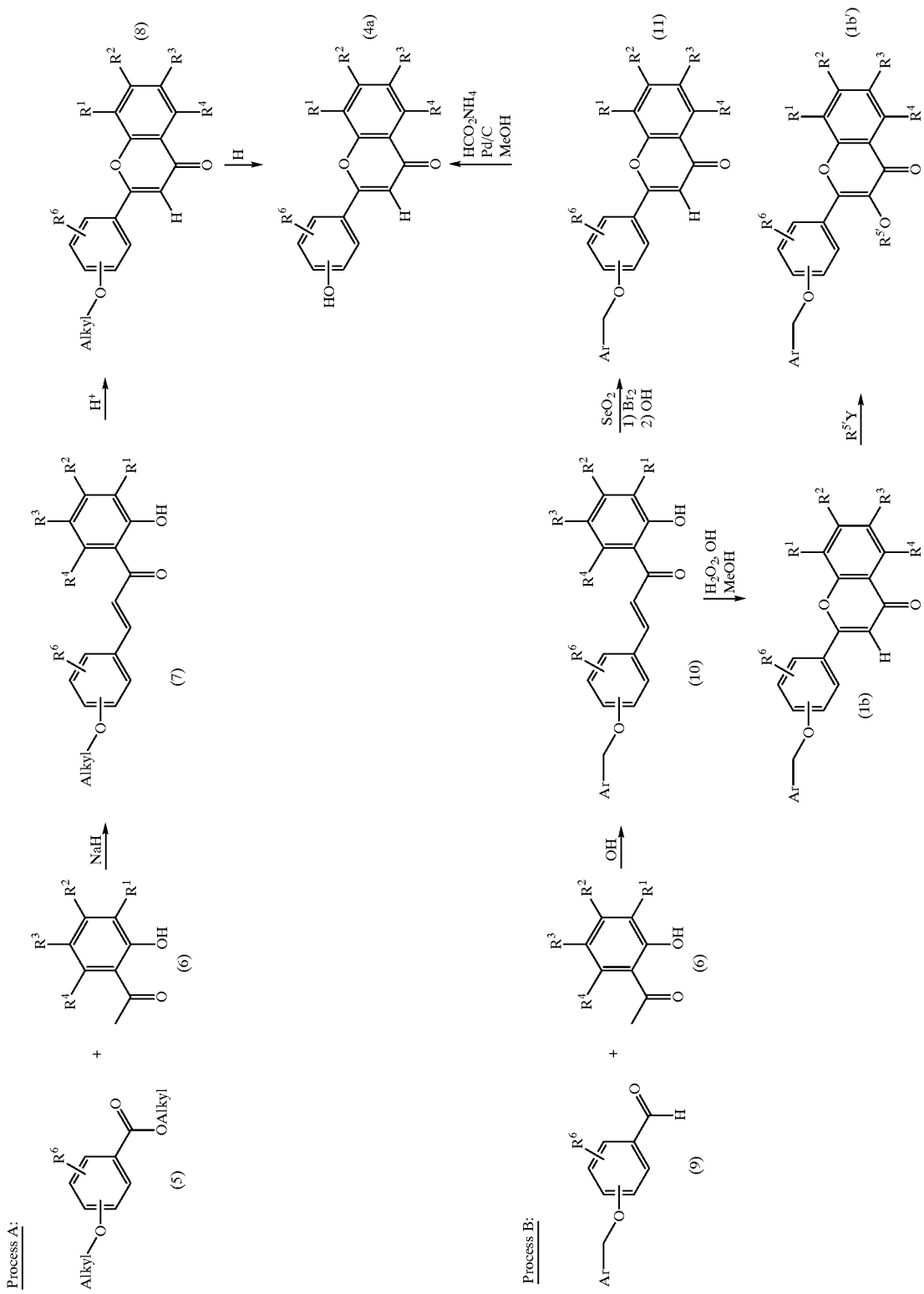

wherein Alkyl represents an alkyl group, Ar represents an aryl group, Me represents a methyl group, $R^{5'}$ represents the same substituent as $R^5$ other than a hydrogen atom, and $R^1$, $R^2$, $R^3$, $R^4$, $R^6$ and Y have the same meanings.

According to the synthesis process A, an alkyl benzoate derivative 5 in which phenolic OH has been protected, for example, by an alkyl group such as methyl or isopropyl and a hydroxyacetophenone derivative (6) are reacted, for example, in the presence of a base such as sodium hydride, whereby a hydroxychalcone derivative (7) is obtained. This hydroxychalcone derivative (7) is converted into a flavone derivative (8) by cyclodehydration. The flavone derivative (8) is deprotected by a method known per se in the art, whereby the hydroxyflavone compound (4a) is obtained.

According to the synthesis process B, on the other hand, a benzaldehyde derivative (9) in which phenolic OH has been protected, for example, by a protecting group removable under mild conditions, such as a benzyl group and a hydroxyacetophenone derivative (6) are reacted, for example, in a solvent such as ethanol, THF (tetrahydrofuran) or water in the presence of a base such as sodium hydroxide or potassium hydroxide, whereby a hydroxychalcone derivative (10) is obtained. This hydroxychalcone derivative (10) can be converted into a flavone derivative (11; invention compound), for example, by subjecting it to dehydration in the presence of an oxidizing agent such as selenium dioxide or by dihalogenating it, for example, with bromine and then subjecting the resultant dihalochalcone to dehydrohalogenation. The flavone derivative (11) can be converted into the hydroxyflavone derivative (4a), for example, by subjecting it to catalytic reduction by a palladium catalyst or the like in the presence of ammonium formate in methanol.

Among the compounds (1a) of the present invention, compounds (1b) in which $R^5$ is OH can each be obtained by treating the hydroxychalcone derivative (10) with hydrogen peroxide in the presence of a base. Further, the compound (1b) can be converted into a compound with an aminoalkyl group as $R^{5'}$, for example, by subjecting it to alkylation with a haloalkylphthalimide in the presence of potassium carbonate in DMF and then hydrolyzing the alkylated derivative with hydrazine. The thus-obtained amine compound can be converted into a compound with a dimethylaminoalkyl group as $R^{5'}$ by reacting it with formaldehyde in the presence of cyanosodium borohydride. Further, the compound (1b) can be converted into an invention compound with an aralkylpiperazylalkyl group or an aralkylhomopiperazylalkyl group as $R^{5'}$ by haloalkylating the compound (1b) through a reaction with Z—$(CH_2)_n$—Z, in which Z represents a chlorine atom, a bromine atom or an iodine atom and n stands for 1 to 5, in the presence of potassium carbonate in acetone (if one or more of $R^1$ to $R^4$ are carboxyl groups, general ethyl esterification should be conducted beforehand by an acid catalyst, for example, in ethanol) and then reacting the haloalkylated derivative with an N-aralkylpiperazine (or homopiperazine).

On the other hand, the compound (5) in the reaction scheme can be obtained in a manner known per se in the art, for example, by reacting an appropriate alkyl hydroxybenzoate and a suitable alkyl halide in the presence of potassium carbonate in acetone or DMF. The compound (9) can also be obtained by a similar reaction between an adequate hydroxybenzaldehyde derivative and an appropriate benzyl halide.

Among compounds (6), those containing a carboxyl group or cyano group as at least one of $R^1$ to $R^4$ can each be obtained by a known method (Doria, G. et al. Eur. J. Med. Chem.-Chim. Ther., 13, 33–39, 1978; Wurm, G. et al. Arch. Pharm. 310, 119–128, 1977), namely, by Fries rearrangement from a compound (12), i.e., an acetyl derivative.

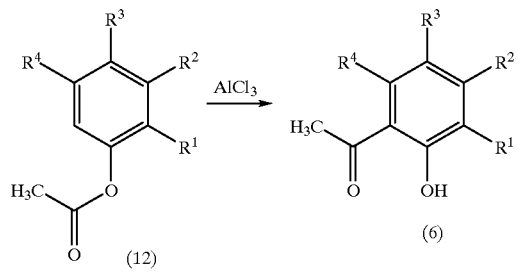

wherein $R^1$, $R^2$, $R^3$ and $R^4$ have the same meanings as defined above.

Next, among the compounds (1) according to the present invention, compounds (1c) in which W is —C=C— and $R^5$ is a hydrogen atom can each be prepared by the following process which is similar to the above-described synthesis process B.

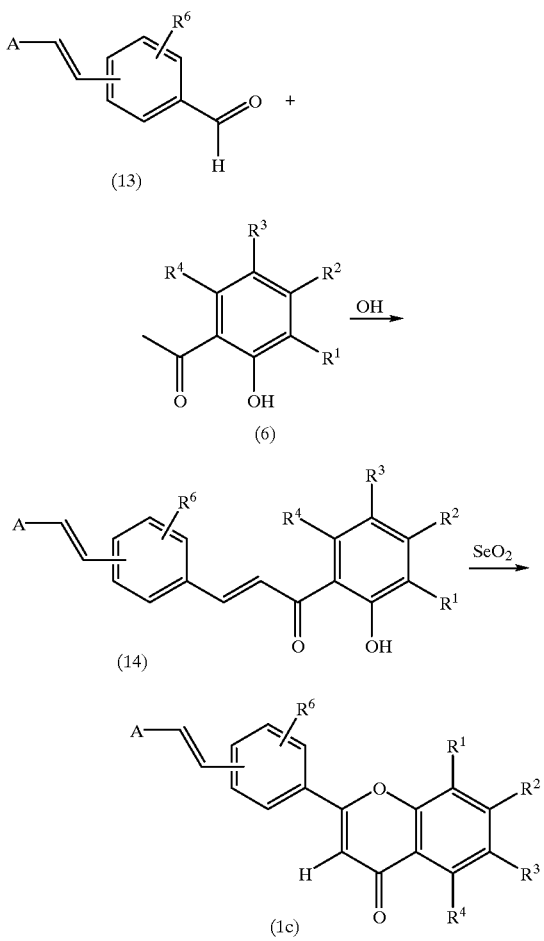

wherein A, $R^1$, $R^2$, $R^3$, $R^4$, and $R^6$ have the same meanings as defined above.

Described specifically, a hydroxychalcone derivative (14) is obtained by Claisen-Schmidt condensation between a benzaldehyde derivative (13) and a hydroxyacetophenone derivative (6). The hydroxychalcone derivative is then subjected to dehydrogenation with selenium dioxide, whereby the invention compound (1c) is obtained. The benzaldehyde derivative (13) is obtained by heating benzenedialdehyde (phthalaldehyde or its isomer) and a methylated aromatic compound together with acetic anhydride in a solvent such as xylene.

Among the invention compounds (1a), (1b), (1b'), (1c) and (11) or the compounds (4), (6), (7), (8), (10), (12) and (14), those containing an alkyloxycarbonyl group or a tetrazolyl group as at least one of $R^1$ to $R^4$ can each be obtained from a corresponding carboxylic acid derivative or nitrile derivative by a method known per se in the art. For example, by refluxing a carboxylic acid derivative (in which at least one of $R^1$ to $R^4$ represents a carboxyl group) together with 5% of sulfuric acid in alcohol, the corresponding ester (in which at least one of $R^1$ to $R^4$ represents an alkyloxycarbonyl group) can be obtained. Further, by reacting a nitrile derivative (in which at least one of $R^1$ to $R^4$ represents a cyano group) with sodium azide in the presence of ammonium chloride in DMF, the corresponding tetrazole derivative (in which at least one of $R^1$ to $R^4$ represents a tetrazolyl group) can be obtained. In addition, an amide derivative (in which at least one of $R^1$ to $R^4$ represents $CONHR^8$, $R^8$ having the same meaning as defined above) can be obtained, for example, by subjecting a carboxylic acid derivative (in which at least one of $R^1$ to $R^4$ represents a carboxyl group) and an amino compound to condensation, for example, with a dehydrating condensing agent such as dicyclohexylcarbodiimide.

The compound (1) according to the present invention can be obtained by the above-described process. Further, it can be purified by a conventional purification method such as recrystallization or column chromatography, as needed. Moreover, it can be converted into the above-described desired salt by a method known per se in the art, as needed.

The invention compound (1) or its salt obtained as described above has excellent cys-$LT_1$ receptor antagonism and leucotriene inhibitory activities as will be indicated in tests to be described subsequently herein, and is therefore useful as medicine for the prevention or therapy of various allergic diseases and inflammatory diseases such as asthma, allergic rhinitis, allergic dermatitis, allergic conjunctivitis, urticaria, psoriasis, rheumatism, inflammatory colitis, cerebral ischemia or cerebral apoplexy.

A medicine according to the present invention comprises the above-described compound (1) as an effective ingredient. Its administration form is not limited in particular, but can be suitably chosen in accordance with the object of a therapy, for example, can be in the form of any one of oral preparations, injections, suppositories, ointments, inhalative agents, eye drops, nasal drops, plasters and the like. These administration forms can each be prepared by a preparation method commonly known and used by those skilled in the art.

To produce an oral solid preparation, an excipient and if necessary, a binder, a disintegrator, a lubricant, a coloring matter, a taste corrigent, a smell corrigent and/or the like are added to the compound (1) of the present invention. The resulting mixture can then be formed into tablets, coated tablets, granules, powder, capsules or the like by a method known per se in the art. Such additives can be those generally employed in the present field of art, including excipients: lactose, sucrose, sodium chloride, glucose, starch, calcium carbonate, kaolin, microcrystalline cellulose, and silicic acid; binders: water, ethanol, propanol, suclose solution, glucose solution, starch solution, gelatin solution, carboxymethylcellulose, hydroxypropylcellulose, hydroxypropylstarch, methylcellulose, ethylcellulose, shellac, calcium phosphate, and polyvinylpyrrolidone; disintegrators: dry starch, sodium alginate, powdered agar, sodium hydrogencarbonate, calcium carbonate, sodium lauryl sulfate, monoglycerol stearate, and lactose; lubricants: purified talc, stearate salts, borax, and polyethylene glycol; corrigents: sucrose, bitter orange peel, citric acid, and tartaric acid.

To produce an oral liquid preparation, a taste corrigent, a buffer, a stabilizer, a smell corrigent and the like are added to the compound (1) of the present invention. The resulting mixture can then be formed into a solution for internal use, a syrup, an elixir or the like by a method known per se in the art. In this case, the taste corrigent can be the same as that mentioned above. Illustrative of the buffer is sodium citrate, while illustrative of the stabilizer are tragacanth, gum arabic, and gelatin.

To prepare an injection, a pH regulator, a buffer, a stabilizer, an isotonicity, a local anesthetic and the like are added to the compound (1) of the present invention. The resulting mixture can then be formed into a subcutaneous, intramuscular or intravenous injection by a method known per se in the art. Examples of the pH regulator and buffer include sodium citrate, sodium acetate, and sodium phosphate. Illustrative of the stabilizer include sodium pyrosulfite, EDTA, thioglycollic acid, and thiolactic acid. Illustrative of the local anesthetic are procaine hydrochloride and lidocaine hydrochloride. Examples of the isotonicity include sodium chloride and glucose.

To prepare suppositories, a pharmaceutical carrier known in the present field of art, for example, polyethylene glycol, lanolin, cacao butter or fatty acid triglyceride is added optionally together with a surfactant such as "Tween" (registered trademark) to the compound (1) of the present invention. The resulting mixture can then be formed into suppositories by a method known per se in the art.

To prepare an ointment, a pharmaceutical base, a stabilizer, a humectant, a preservative and the like are combined, as needed, with the compound (1) of the present invention. The resultant mixture can then be mixed and prepared into an ointment by a method known per se in the art. Illustrative of the pharmaceutical base are liquid paraffin, white petrolatum, white beewax, octyldodecyl alcohol, and paraffin. Examples of the preservative include methyl parahydroxybenzoate, ethyl parahydroxybenzoate, and propyl parahydroxybenzoate.

In addition to the above-described preparations, the compound (1) of the present invention can also be formed into an inhalative agent, an eye drop and a nasal drop by methods known per se in the art.

The dosage of the medicine according to the present invention varies depending on the age, body weight, conditions, administration form, administration frequency and the like. In general, however, it is preferred to orally or parenterally administer to an adult the effective ingredient in an amount of about 1 to 1,000 mg per day at once or in several portions.

The present invention will next be described in further detail by the following Examples. It should however be borne in mind that the present invention is by no means limited to these Examples.

PREPARATION EXAMPLE 1

Synthesis of 5-bromo-3-carboxy-2-hydroxyacetophenone 1) 5-Bromosalicylic acid (100 g, 0.46 mol) and acetic anhydride (105 ml) were combined, to which 0.5 ml of concentrated sulfuric acid was added. The resulting mixture solidified in several minutes. Subsequent to suspension in 1,000 ml of water, the solid matter was collected by filtration and then washed with water. The thus-obtained white powder was dried in air and then dissolved in 1,000 ml of ethyl acetate. The ethyl acetate layer was washed with a saturated aqueous solution of sodium chloride and then dried over anhydrous sodium sulfate. Subsequent to concentration under reduced pressure, 105 g of 2-acetoxy-5-bromobenzoic acid were obtained as white crystals (yield: 89%).

2) 2-Acetoxy-5-bromobenzoic acid (100 g, 0.39 mol) and aluminum chloride (159 g, 1.20 mol) were combined, followed by stirring at 160° C. for 3 hours. After the resulting mixture was allowed to cool down to room temperature, the resulting solid matter was crushed into the form of mortar and then charged into a mixture of 200 ml of concentrated hydrochloric acid and 800 g of water. The resulting slurry-like mixture was extracted with ethyl acetate. The ethyl acetate layer was washed with 1 N hydrochloric acid and a saturated aqueous solution of sodium chloride, dried over anhydrous sodium sulfate, and then concentrated under reduced pressure. Crude crystals were washed with dichloromethane to eliminate byproducts and, subsequent to drying in air, 36.4 g of the title compound were obtained as pale brown powder (yield: 36%).

m.p.: 200.1° C.

| | |
|---|---|
| $^1$H-NMR(DMSO-d$_6$); | δ2.59(3H, s, CH$_3$CO), 7.92(1H, d, J=2.7Hz, C4-H), 8.01(1H, d, J=2.7Hz, C6-H), 11.64(2H, br.s, OH and COOH). |

PREPARATION EXAMPLE 2

Synthesis of 3-carboxy-5-chloro-2-hydroxyacetophenone

In a similar manner as in Preparation Example 1, the title compound was obtained in two steps from 5-chlorosalicilic acid (yield: 45%).

m.p.: 173.7–175.8° C.

| | |
|---|---|
| $^1$H-NMR(DMSO-d$_6$); | δ2.60(3H, s, CH$_3$CO), 7.84(1H, d, J=2.7Hz, C6-H), 7.92(1H, d, J=2.7Hz, C4-H), 12.28(2H, br.s, OH and COOH). |

PREPARATION EXAMPLE 3

Synthesis of 3-carboxy-5-fluoro-2-hydroxyacetophenone

In a similar manner as in Preparation Example 1, the title compound was obtained in two steps from 5-fluorosalicilic acid (yield: 35%).

m.p.: 156.8–159.2° C.

| | |
|---|---|
| $^1$H-NMR(DMSO-d$_6$); | δ2.61(3H, s, CH$_3$CO), 7.66–7.79(2H, m, C3-H, C5-H), 11.88(2H, br.s, OH and COOH). |

PREPARATION EXAMPLE 4

Synthesis of 3-carboxy-2-hydroxy-5-methylacetophenone

In a similar manner as in Preparation Example 1, the title compound was obtained in two steps from 5-methylsalicilic acid (yield: 82%).

m.p.: 122.2–125.8° C.

| | |
|---|---|
| $^1$H-NMR(DMSO-d$_6$); | δ2.32(3H, s, CH$_3$), 2.67(3H, s, CH$_3$CO), 7.77(1H, d, J=2.3Hz, C3-H/C5-H), 8.05(1H, d, J=2.3Hz, C3-H/C5-H), 9.25(1H, br.s, COOH), 13.45(1H, br.s, OH). |

PREPARATION EXAMPLE 5

Synthesis of 3-carboxy-2-hydroxyacetophenone

5-Bromo-3-carboxy-2-hydroxyacetophenone (10.0 g, 38.6 mmol) was dissolved in 75 ml of ethanol, followed by the addition of 1.0 g of 10% palladium-carbon. The resultant mixture was subjected to catalytic hydrogenation under a pressure of 15 atm at room temperature for 2 hours. Subsequent to removal of the catalyst, the filtrate was neutralized with 2 N aqueous solution of sodium hydroxide and then concentrated under reduced pressure. The thus-obtained, slightly grayish solid was dissolved in 1 N aqueous solution of sodium hydroxide, to which 3 N hydrochloric acid was added. The resulting precipitate was collected by filtration and then washed with water. Subsequent to drying in air, 6.8 g of the title compound were obtained as a white solid (yield: 98%).

m.p.: 131.8–133.0° C.

$^1$H-NMR(DMSO-d$_6$); δ2.63(3H, s, CH$_3$CO), 7.03(1H, t, J=7.8Hz, C5-H),7.94(1H, dd, J=7.8Hz, 1.8Hz, C4-H), 8.03(1H, dd, J=7.8Hz, 1.8Hz, C6-H).

PREPARATION EXAMPLE 6

Synthesis of 3-cyano-5-chloro-2-hydroxyacetophenone 1) 2-Amino-4-chlorophenol (50 g, 0.35 mol) was dissolved in 500 ml of 2.5 N hydrochloric acid, to which an aqueous solution of 25.25 g (0.37 mol) of sodium nitrite in 50 ml of water was gradually added dropwise with cooling at 0° C. After stirring for 30 minutes, the reaction mixture was confirmed to show "positive" in an iodostarch reaction and an aqueous solution of 70 g (0.42 mol) of sodium iodide in 100 ml of water was added slowly. The temperature of the reaction mixture was allowed to rise to room temperature, at which the reaction mixture was stirred overnight and then extracted with ethyl acetate. The ethyl acetate layer was concentrated, whereby 89.7 g of 4-chloro-2-iodophenol were obtained as a purple solid (yield: 99%).

2) 4-Chloro-2-iodophenol (85 g, 0.33 mol) was dissolved in 150 ml of DMF, followed by the addition of 32.5 g (0.36 mol) of copper cyanide. The resulting mixture was refluxed for 2 hours and then concentrated under reduced pressure. The residue was dissolved in ethyl acetate, and the thus-prepared solution was washed with water. Subsequent to elimination of an undissolved salt, the solution was concentrated under reduced pressure, whereby 40.4 g of 5-chloro-2-hydroxybenzonitrile were obtained (yield: 80%). Without purification, it was provided for use in the next step.

3) 5-Chloro-2-hydroxybenzonitrile (39.25 g, 0.25 mol) and acetic anhydride (40 ml) were combined, to which 0.5 ml of concentrated sulfuric acid was added. The reaction mixture was stirred at 60° C. for 10 minutes, followed by the addition of water. Subsequent to extraction with ethyl acetate, the organic layer was washed with 1 N aqueous solution of sodium hydroxide and a saturated aquous solution of sodium chloride, dried over anhydrous sodium sulfate, and then concentrated under reduced pressure, whereby 45 g of 2-acetoxy-5-chlorobenzonitrile were obtained as a brown solid (yield: 92%). It was provided for immediate use in the next step.

4) 2-Acetoxy-5-chlorobenzonitrile (44 g, 0.23 mol) and aluminum chloride (99 g, 0.75 mol) were combined, followed by stirring at 160° C. for 3 hours. After the reaction mixture was allowed to cool down to room temperature, the resulting solidified mixture was ground into the form of mortar, and then charged into 100 ml of concentrated hydrochloric acid in which ice had been added. The resulting slurry was extracted with ethyl acetate. The extract was washed with 1 N hydrochloric acid and a saturated aqueous solution of sodium chloride, dried over anhydrous sodium sulfate, and then concentrated under reduced pressure. To eliminate byproducts contained in trace amounts in the crystalline residue, the crystalline residue was washed with dichloromethane, whereby 16.5 g of the title compound were obtained as a brown solid (yield: 38%).

m.p.: 137.9–139.8° C.

$^1$H-NMR(DMSO-d$_6$); δ2.72(3H, s, CH$_3$CO), 8.21(1H, d, J=2.5Hz, C4-H)/C6-H), 8.32(1H, d, J=2.5Hz, C4-H/C6-H), 12.77(1H, br.s, ArOH).

PREPARATION EXAMPLE 7

Synthesis of methyl 3-isopropoxybenzoate

Methyl 3-hydroxybenzoate (1 eq.) and 2-bromopropane (2 eq.) were dissolved in DMF. Subsequent to addition of potassium carbonate (2 eq.), the resulting mixture was stirred at 100° C. for 24 hours. The mixture was charged into water. Subsequent to extraction with ethyl acetate, the organic layer was washed with 1 N aqueous solution of sodium hydroxide and a saturated aqueous solution of sodium chloride, dried over anhydrous sodium sulfate, and then concentrated under reduced pressure, whereby the title compound was obtained (yield: 49%).

$^1$H-NMR(CDCl$_3$); δ1.32(6H, d, J=6.0Hz, CH(C$\underline{H}_3$)$_2$), 3.88(3H, s, CO$_2$CH$_3$), 4.59(1H, h, J=6.0Hz, C$\underline{H}$(CH$_3$)$_2$), 7.05(1H, dd, J=8.2Hz, 2.6Hz, C4-H), 7.30(1H, t, J=7.9Hz, C5H), 7.52(1H, m, C2-H), 7.57(1H, dd, J=7.6Hz, 1.6Hz, C6-H).

PREPARATION EXAMPLE 8

Synthesis of ethyl 4-isopropoxybenzoate

In a similar manner as in Preparation Example 7, the title compound was obtained from ethyl 4-hydroxybenzoate (yield: 37%).

$^1$H-NMR(CDCl$_3$); δ1.33(6H, d, J=6.0Hz, CH(C$\underline{H}_3$)$_2$), 1.35(3H, t, J=7.3Hz, CO$_2$CH$_2$C$\underline{H}_3$), 4.32(2H, q, J=7.3Hz, CO$_2$C$\underline{H}_2$CH$_3$), 4.61(1H, h, J=6.4Hz, C$\underline{H}$(CH$_3$)$_2$), 6.86(2H, dd, J=8.9Hz, C3-H, C5-H), 7.95(2H, d, J=8.9Hz, C2-H, C6-H).

PREPARATION EXAMPLE 9

Synthesis of 4-(2-quinolinylmethoxy)benzaldehyde

2-Chloromethylquinoline hydrochloride (6.42 g, 30 mmol), 4-hydroxybenzaldehyde (3.66 g, 30 mmol) and potassium carbonate (9.12 g, 66 mmol) were combined, to which 50 ml of DMF were added. The resulting mixture was stirred overnight at 90° C. The solvent was driven off under reduced pressure, the residue was extracted with ethyl acetate. The organic layer was washed with 1 N aqueous solution of sodium hydroxide and a saturated aqueous solution of sodium chloride, dried over anhydrous sodium sulfate, and then concentrated under reduced pressure, whereby 7.19 g of the title compound were obtained (yield: 91%).

m.p.: 81.0–82.1° C.

| $^1$H-NMR(CDCl$_3$); | δ5.41(2H, s, C$_9$H$_6$NC$\underline{H}_2$O), |
| --- | --- |
| | 7.10(2H, d, J=8.7Hz, C3-H, C5-H) |
| | 7.47–7.51(1H, m, quinoline C6-H), |
| | 7.58(1H, d, J=8.5Hz, quinoline C3-H), |
| | 7.67–7.71(1H, m, quinoline C7-H), |
| | 7.74–7.79(1H, m, quinoline C5-H), |
| | 7.79(2H, d, J=8.7Hz, C4-H, C6-H), |
| | 8.07(1H, d, J=8.3Hz, quinoline C8-H), |
| | 8.15(1H, d, J=8.5Hz, quinoline C4-H), |
| | 9.86(1H, s, CHO). |

PREPARATION EXAMPLE 10

Synthesis of 3-(2-quinolinylmethoxy)benzaldehyde

In a similar manner as in Preparation Example 9, the title compound was obtained from 3-hydroxybenzaldehyde (yield: 61%).

m.p.: 55.1–57.1° C.

| $^1$H-NMR(CDCl$_3$); | δ5.35(2H, s, C$_9$H$_6$NC$\underline{H}_2$O), 7.20(1H, m, C4-H), |
| --- | --- |
| | 7.36–7.47(3H, m, quinoline C5-H, |
| | quinoline C6-H, C5-H), |
| | 7.64–7.69(1H, m, quinoline C7-H), |
| | 7.72–7.76(1H, m, C6-H), |
| | 8.01(1H, d, J=8.3Hz, quinoline C8-H), |
| | 8.11(1H, d, J=8.5Hz, quinoline C4-H), |
| | 9.87(1H, s, CHO). |

PREPARATION EXAMPLE 11

Synthesis of 4-[2-(2-quinolinyl)ethenyl]benzaldehyde 1,4-Benzenedialdehyde (30 g, 0.22 mol), 2-methylquinoline (21 g, 0.15 mol) and acetic anhydride (41.5 ml, 0.40 mol) were dissolved in 160 ml of xylene. The resulting mixture was refluxed for 7 hours. After the mixture was allowed to cool down to room temperature, it was added to 200 ml of petroleum ether which had been warmed to 40–60° C. The resulting precipitate was filtered off. The mother liquor was concentrated and the crude product so obtained was recrystallized twice from etnanol, whereby 13.6 g of the title compound were obtained (yield: 35%).

m.p.: 111.9–113.0° C.

| $^1$H-NMR(CDCl$_3$); | δ7.46–7.51(2H, m, Ar-H), |
| --- | --- |
| | 7.54-7.80(6H, m, Ar-H, olefin-H), |
| | 7.87-7.91(2H, m, Ar-H), |
| | 8.08(1H, d, J=8.4Hz, Ar-H), |
| | 8.14(1H, d, J=8.6Hz, quinoline C4-H), |
| | 10.00(1H, s, CHO). |

PREPARATION EXAMPLE 12

Synthesis of 3-[2-(2-quinolinyl)ethenyl]benzaldehyde

Using 1,3-benzenedialdehyde, a reaction was conducted as in Example 11. Subsequent to the completion of the reaction, the reaction mixture was concentrated under reduced pressure and then dissolved in ethyl acetate. The thus-obtained solution was washed with 1 N aqueous solution of sodium hydroxide and a saturated aqueous solution of sodium chloride, dried over anhydrous sodium sulfate, and then concentrated under reduced pressure. The resulting brown oil was dissolved in hot ethanol, followed by cooling. After the resulting first crystals (by-products) were removed, the mother liquor was concentrated. The concentrate was then recrystallized twice from ethanol, whereby 18.6 g of the title compound were obtained in a purified form (yield: 48%).

m.p.: 78.6–80.8° C.

| $^1$H-NMR(DMSO-d$_6$); | δ7.42–7.89(9H, m, Ar-H, olefin-H), |
| --- | --- |
| | 8.08–8.16(3H, m, Ar-H), 10.04(1H, s, CHO). |

PREPARATION EXAMPLE 13

Synthesis of 6-bromo-8-ethoxycarbonyl-3'-hydroxyflavone

1) Sodium hydride (6 eq.) was suspended in dioxane, to which a solution of methyl 3-isopropoxybenzoate (3 eq.) and 5-bromo-3-ethoxycarbonyl-2-hydroxyacetophenone (1 eq.) in dioxane was gradually added dropwise. The resulting mixture was refluxed for 7 hours and then allowed to cool down to room temperature. Petroleum ether was then added. The resulting precipitate was collected by filtration and then dissolved in water. The aqueous solution was acidified, whereby 1-(5-bromo-3-ethoxycarbonyl-2-hydroxyphenyl)-3-(3-isopropoxy)phenyl-1,3-propanedione was obtained (yield: 50%). Without purification, it was provided for use in the next reaction.

m.p.: 65.9–66.3° C.

2) 1-(5-Bromo-3-ethoxycarbonyl-2-hydroxyphenyl)-3-(3-isopropoxy)phenyl-1,3-propanedione was dissolved in 99% formic acid, followed by refluxing for 1 to 2 hours. After the mixture was allowed to cool down, ice water was added. The resulting precipitate was collected by filtration. The crude product was recrystallized from ethanol, whereby 6-bromo-8-ethoxycarbonyl-3'-isopropoxyflavone was obtained as white crystals (yield: 80%).

| $^1$H-NMR(CDCl$_3$); | δ1.40(6H, d, J=6.0Hz, OCH(C$\underline{H}_3$)$_2$), |
| --- | --- |
| | 1.49(3H, t, J=7.1Hz, CO$_2$CH$_2$C$\underline{H}_3$), |
| | 4.51(2H, q, J=7.1Hz, CO$_2$C$\underline{H}_2$CH$_3$), |
| | 4.68(1H, h, J=6.0Hz, OC$\underline{H}$(CH$_3$)$_2$), |
| | 6.88(1H, s, C3-H), |
| | 7.06–7.10(1H, m, C4'-H), 7.43(1H, t, J=8.0Hz, C5'-H), |
| | 7.58–7.65(2H, m, C2'-H, C6'-H), |
| | 8.39(1H, d, J=2.6Hz, C5-H/C7-H), |
| | 8.54(1H, d, J=2.6Hz, C5-H/C7-H). |

3) 6-Bromo-8-ethoxycarbonyl-3'-isopropoxyflavone were refluxed under heat for 0.5 to 1 hour in acetic acid which contained 3% of sulfuric acid. The mixture was charged into ice water, followed by extraction with ethyl acetate. The organic layer was washed with water and 4% aqueous solution of sodium hydrogencarbonate, dried over anhydrous sodium sulfate, and then concentrated under reduced pressure. The thus-obtained crude crystals were recrystallized from ethanol, whereby the title compound was obtained (yield: 80%).

m.p.: 242.3–243.6° C.

| | |
|---|---|
| $^1$H-NMR(CDCl$_3$); | δ1.47(3H, t, J=7.1Hz, CO$_2$CH$_2$C$\underline{H}_3$), |
| | 4.48(2H, q, J=7.1Hz, CO$_2$C$\underline{H}_2$CH$_3$), |
| | 6.07(1H, br.s, OH), |
| | 7.01(1H, s, C3-H), 7.04–7.06 (1H, m, C4'-H) |
| | 7.39(1H, t, J=8.0Hz, C5'-H), |
| | 7.57–7.60 (2H, m, C2'-H, C6'-H), |
| | 8.38(1H, d, J=2.6Hz, C5-H/C7-H), |
| | 8.52(1H, d, J=2.6Hz, C5-H/C7-H). |

PREPARATION EXAMPLE 14

Synthesis of 3'-hydroxy-8-ethoxycarbonylflavone

3'-Benzyloxy-8-ethoxycarbonylflavone (1 eq.) was dissolved in methanol, followed by the addition of ammonium formate (8 eq.) and 10% wt/wt palladium-carbon. The resulting mixture was refluxed. Subsequent to the completion of the reaction, the catalyst was eliminated by hot filtration. The mother liquor was allowed to cool down to room temperature. The resulting crystals were collected by filtration, washed with water and then recrystallized from DMF-ethanol, whereby the title compound was obtained (yield: 51%).

m.p.: 224.5–225.5° C.

| | |
|---|---|
| $^1$H-NMR(DMSO-d$_6$); | δ1.40(3H, t, J=7.1Hz, CO$_2$CH$_2$C$\underline{H}_3$), |
| | 4.45(2H, q, J=7.1Hz, CO$_2$C$\underline{H}_2$CH$_3$), |
| | 7.00–7.02(1H, m, C4'-H), |
| | 7.04(1H, s, C3-H), |
| | 7.34–7.42(1H, m, C6-H), |
| | 7.55–7.62(3H, m, C2'-H, C5'-H, C6'-H), |
| | 8.27–8.31(2H. m, C5-H, C7-H, |
| | 9.91(1H, br.s, Ar-OH). |

PREPARATION EXAMPLE 15

Synthesis of 4'-hydroxy-8-ethoxycarbonylflavone

In a similar manner as in Preparation Example 14, the title compound was obtained from 4'-benzyloxy-8-ethoxycarbonylflavone (yield: 62%).

m.p.: 250.3–251.2 ° C.

| | |
|---|---|
| $^1$H-NMR(DMSO-d$_6$); | δ1.40(3H, t, J=7.1Hz, CO$_2$CH$_2$C$\underline{H}_3$), |
| | 4.44(2H, q, J=7.1Hz, CO$_2$C$\underline{H}_2$CH$_3$), |
| | 6.93(2H, d, J=8.8Hz, C3'–H, C5'–H), |
| | 6.94(1H, s, C3-H), |
| | 7.53(1H, t, J=7.7Hz, C6-H), |
| | 8.03(2H, d, J=8.8Hz, C2'-H, C6'-H), |
| | 8.25(2H, d, J=8.0Hz, C5-H, C7-H). |

EXAMPLE 1

Synthesis of 4'-benzyloxy-6-carboxyflavone

1) Equimolar amounts of 4-(benzyloxycarbonyl) benzaldehyde and 5-carboxy-2-hydroxyacetophenone were dissolved in ethanol, followed by the addition of 25% potassium hydroxide solution. The reaction mixture was stirred at room temperature for 1 week and then charged into ice water. After 3 N hydrochloric acid was added to the resulting mixture to acidify the same, the resulting yellow precipitate was collected by filtration and then dried in air. The crude crystals so obtained were recrystallized from ethanol-DMF, whereby 4-benzyloxy-3'-carboxy-2'-hydroxychalcone was obtained (yield: 45%)

m.p.: 173.8–174.9° C.

| | |
|---|---|
| $^1$H-NMR(DMSO-d$_6$); | δ5.16(2H, s, C$_6$H$_5$C$\underline{H}_2$O), |
| | 7.02(1H, t, J=7.7Hz, C5'-H), |
| | 7.07(2H, d, J=8.7Hz, C6-H, C8-H), |
| | 7.29–7.47(5H, m, C$_6$$\underline{H}_5$CH$_2$O), |
| | 7.54(1H, d, J=15.8Hz, Ha), |
| | 7.64(1H, d, J=15.8Hz, Hb), |
| | 7.74(2H, d, J=8.7Hz, C5-H, C9H), |
| | 7.92(1H, dd, J=7.7Hz, 1.8Hz, C5-H/C7-H), |
| | 8.00(1H, dd, J=7.7Hz, 1.8Hz, C5-H/C7-H). |

2) Dioxane was added to 4-benzyloxy-3'-carboxy-2'-hydroxychalcone (1 eq.) and selenium dioxide (2.2 eq.), followed by refluxing for 8 hours. The resulting mixture was purified by chromatography on a short silica gel column while it was still hot, whereby the title compound represented by the following formula was obtained (yield: 49%).

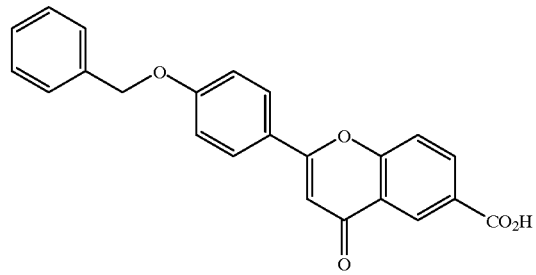

m.p.: 251.8–253.9 ° C.

| | |
|---|---|
| $^1$H-NMR(DMSO-d$_6$); | δ5.21(2H, s, C$_6$H$_5$C$\underline{H}_2$O), |
| | 7.00(1H, s, C3-H), 7.18(2H, d, J=8.9Hz, C3'-H, CS'-H), |
| | 7.33–7.49(5H, m, C$_6$$\underline{H}_5$CH$_2$O), |
| | 7.84(1H, d, J=8.7Hz, C8-H), |
| | 8.07(2H, d, J=8.9Hz, C2'-H, C6'-H), |
| | 8.27(1H, dd, J=8.7Hz, 2.1Hz, C7-H), |
| | 8.55(1H, d, J=2.1Hz, C5-H), |
| | 13.20(1H, br.s, ArCOOH). |

EXAMPLE 2

Synthesis of 3'-benzyloxy-8-carboxyflavone

In a similar manner as in Example 1, the title compound represented by the following formula was obtained from 3-(benzyloxycarbonyl)benzaldehyde and 3-carboxy-2-hydroxyacetophenone (yield: 50%).

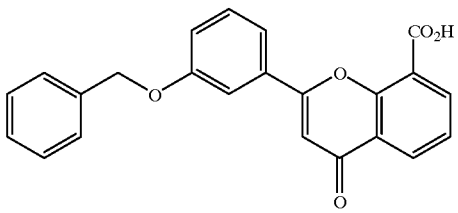

m.p.: 244.8–246.8° C.

| $^1$H-NMR(DMSO-$d_6$); | δ5.20(2H, s, C$_6$H$_5$C$\underline{H}_2$O), 7.22(1H, s, C3-H), 7.24–7.26 (1H, m, C4'-H), 7.44–7.61 (7H, m, C$_6$$\underline{H}_5$CH$_2$O, C6-H, C5'-H), 7.82(1H, d, J=7.8Hz, C6'-H) 7.95(1H, s, C2'-H), 8.26(H, dd, J=7.8Hz, 1.7Hz, C5-H/C7-H), 8.30(1H, dd, J=7.3Hz, 1.7Hz, C5-H/C7-H) |

EXAMPLE 3

Synthesis of 4'-benzyloxy-8-carboxyflavone

In a similar manner as in Example 1, the title compound represented by the following formula was obtained from 4-(benzyloxycarbonyl)benzaldehyde and 3-carboxy-2-hydroxyacetophenone (yield: 80%).

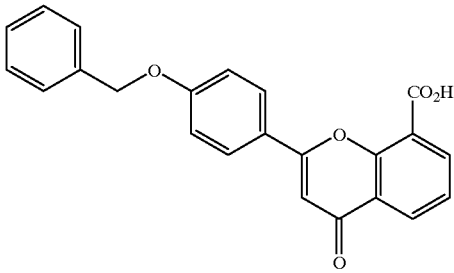

m.p.: 203.2–209.1° C.

| $^1$H-NMR(DMSO-$d_6$); | δ5.22(2H, s, C$_6$H$_5$C$\underline{H}_2$O), 7.06(1H, s, C3-H), 7.19 (2H, d, J=8.9Hz, C3'-H, C5'-H), 7.36–7.54(6H, m, C$_6$$\underline{H}_5$CH$_2$O), C6-H), 8.17(2H, d, J=8.9Hz, C2'-H, C6'-H), 8.21–8.27(2H, m, C5-H, C7-H), 13.50(1H, br.s, COOH). |

EXAMPLE 4

Synthesis of 8-bromo-6-carboxy-4'-[(2-quinolinyl) methoxy]flavone

1) A mixture of 4-(2-quinolinylmethoxy)benzaldehyde (10 mmol) and 5-carboxy-2-hydroxyacetophenone (10 mmol) was dissolved in ethanol, followed by the addition of a 25% aqueous solution of potassium hydroxide. The resulting mixture was stirred at room temperature for 1 week. The reaction mixture was charged into ice water, to which 3 N hydrochloric acid was added for acidification. The resulting precipitate was collected by filtration, washed with water and then recrystallized from ethanol-DMF, whereby 1.28 g of 5'-carboxy-2'-hydroxy-4-(2-quinolinylmethoxy)chalcone were obtained as yellow powder (yield: 30%).

m.p.: 242.7–246.7° C.

| $^1$H-NMR(DMSO-$d_6$); | δ5.47(2H, s, C$_9$H$_6$NC$\underline{H}_2$O), 7.10(1H, d, J=8.7Hz, C3'-H), 7.16(2H, d, J=8.8Hz, C3-H, C5-H), 7.61–7.65(1H, m, quinoline C6-H), 7.69(1H, d, J=8.5Hz, quinoline C3-H), 7.77(1H, d, J=15.6Hz, Hα), 7.77–7.82(1H, m, quinoline C7-H), 7.81(1H, d, J=15.6Hz, Hβ), 7.88(2H, d, J=8.8Hz, C2-H, C6-H), 8.00(1H, d, J=8.2Hz, quinoline C5-H), 8.03–8.05 (2H, m, C4-H, quinoline C8-H), 8.43(1H, d, J=8.5Hz, quinoline C4-H), 8.55(1H, d, J=2.1Hz, C6'-H). |

2) In a solution of 5'-carboxy-2'-hydroxy-4-(2-quinolinylmethoxy)chalcone (1 mmol) in 10 ml of glacial acetic acid, 0.06 ml of bromine was gradually added dropwise. The reaction mixture was stirred at room temperature for 3 hours, and the resulting yellow precipitate was collected and then washed with water. The precipitate was next dissolved in a mixed solvent which was consisted of 8 ml of ethanol and 15 ml of 6% potassium hydroxide. The resulting solution was stirred further for 4 hours. After the reaction mixture was acidified, the resulting precipitate was collected by filtration and then recrystallized from DMF, whereby the title compound represented by the following formula was obtained (yield: 25%).

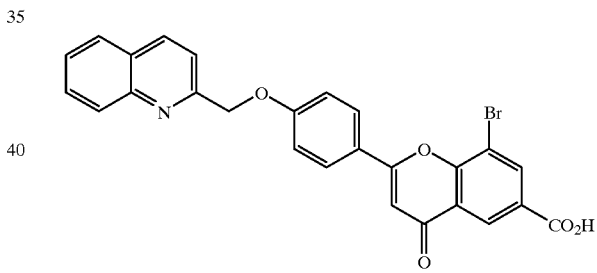

m.p.: >300° C. (Decomposed)

| $^1$H-NMR(DMSO-$d_6$); | δ5.50(2H, s, C$_9$H$_6$NC$\underline{H}_2$O), 7.12(1H, s, C3-H), 7.29(2H, d, J=8.9Hz, C3'-H, C5'-H), 7.59–7.63(1H, m, quinoline C6-H), 7.70(1H, d, J=8.5Hz, quinoline C3-H), 7.76–7.80(1H, m, quinoline C7-H), 7.95–8.05(2H, m, quinoline C5-H, quinoline C8-H), 8.12(2H, d, J=8.9Hz, C2'-H, C6'-H), 8.44(1H, d, J=8.5Hz, quinoline C4-H), 8.46(1H, d, J=2.0Hz, C5-H/C7-H), 8.50(1H, d, J=2.0Hz, C5-H/C7-H), 13.59(1H, br.s, ArCOOH). |

EXAMPLE 5

Synthesis of 6-bromo-8-carboxy-4'-[(2-quinolinyl) methoxy]flavone

In a similar manner as in Example 4, the title compound represented by the following formula was obtained from 4-(2-quinolinylmethoxy)benzaldehyde and 5-bromo-3-carboxy-2-hydroxyacetophenone (yield: 38%).

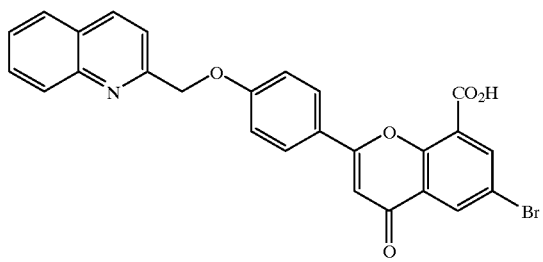

m.p. 261.2–263.9° C.

| | |
|---|---|
| $^1$H-NMR(DMSO-d$_6$); | δ5.43(2H, s, C$_9$H$_6$NCH$_2$O), 7.10(1H, s, C3-H), 7.26(2H, d, J=8.9Hz, C3'-H, C5'-H), 7.60–7.66(1H, m, quinoline C6-H), 7.69(1H, d, J=8.5Hz, quinoline C3-H), 7.75–7.79(1H, m, quinoline C7-H), 7.98–8.05(2H, m, quinoline C5-H, quinoline C8–H), 8.17(2H, d, J=8.9Hz, C2'-H, C6'-H), 8.26(1H, d, J=1.8Hz, C5-H/C7-H), 8.28(1H, d, J=1.8Hz, C5-H/C7-H), 8.43(1H, d, J=8.5Hz, quinoline C4-H). |

EXAMPLE 6

Synthesis of 4'-benzyloxy-6-ethoxycarbonylflavone

4'-Benzyloxy-6-carboxyflavone (1 eq.) was dissolved in HMPA (hexamethylphosphoramide), followed by the addition of sodium hydride (1.1 eq.). Thirty minutes later, ethyl iodide (2 eq.) was added, and the resulting mixture was stirred further for 2 hours at room temperature. The mixture was charged into water, followed by extraction with ethyl acetate. The organic layer was washed with water and a saturated aqueous solution of sodium chloride and then dried over anhydrous sodium sulfate. The solvent was distilled off under reduced pressure, whereby the title compound represented by the following formula was obtained (yield: 25%).

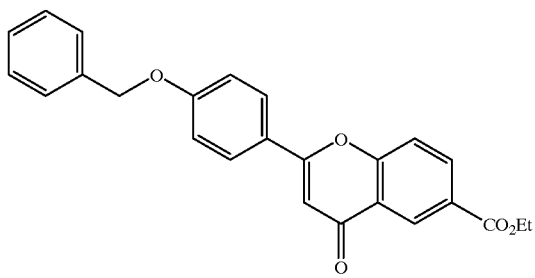

m.p.: 184.3–186.2° C.

| | |
|---|---|
| $^1$H-NMR(CDCl$_3$); | δ1.41(3H, t, J=7.1Hz, CO$_2$CH$_2$CH$_3$), 4.40(2H, q, J=7.1Hz, CO$_2$CH$_2$CH$_3$), 5.14(2H, s, C$_6$H$_5$CH$_2$O), 6.75(1H, s, C3-H), 7.08(2H, d, J=9.0Hz, C3'-H, C5'-H), |

-continued

| | |
|---|---|
| | 7.35–7.42(5H, m, C$_6$H$_5$CH$_2$O), 7.57(1H, d, J=8.7Hz, C8-H), 7.87(2H, d, J=9.0Hz, C2'-H, C6'-H), 8.33(1H, dd, J=8.7Hz, 2.2Hz, C7-H), 8.88(1H, d, J=2.2Hz, C5-H). |

EXAMPLE 7

Synthesis of 3'-benzyloxy-8-ethoxycarbonylflavone

In a similar manner as in Example 6, the title compound represented by the following formula was obtained from 3'-benzyloxy-8-carboxyflavone (yield: 47%).

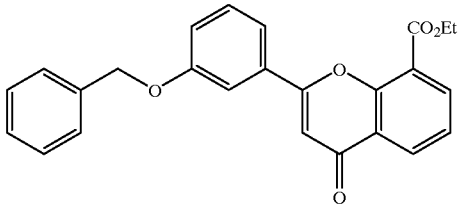

m.p.: 121.0–122.1° C.

| | |
|---|---|
| $^1$H-NMR(CDCl$_3$); | δ1.40(3H, t, J=7.1Hz, CO$_2$CH$_2$CH$_3$), 4.43(2H, q, J=7.1Hz, CO$_2$CH$_2$CH$_3$), 5.12(2H, s, C$_6$H$_5$CH$_2$O), 6.81(1H, s, C3-H), 7.09(1H, dd, J=8.3Hz, 2.5Hz, C4'-H), 7.27–7.44(7H, m, C5'-H, C8-H, C$_6$H$_5$CH$_2$O), 7.59–7.63(1H, m, C6'-H), 7.70–7.71(1H, br.s, C2'-H), 8.26(1H, dd, J=7.6Hz, 1.8Hz, C5-H/C7-H), 8.37(1H, dd, J=7.9Hz, 1.8Hz, C5-H/C7-H). |

EXAMPLE 8

Synthesis of 4'-benzyloxy-8-ethoxycarbonylflavone

In a similar manner as in Example 6, the title compound represented by the following formula was obtained from 4'-benzyloxy-8-carboxyflavone (yield: 76%).

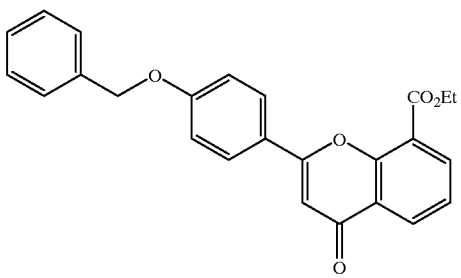

m.p.: 145.1–147.1° C.

| | |
|---|---|
| $^1$H-NMR(CDCl$_3$); | δ1.45(3H, t, J=7.1Hz, CO$_2$CH$_2$CH$_3$), 4.48(2H, q, J=7.1Hz, CO$_2$CH$_2$CH$_3$), |

-continued 5.13(2H, s, C₆H₅CH₂O), 6.79(1H, s, C3-H),
7.08(2H, d, J=9.0Hz, C3'-H, C5'-H),
7.31–7.46(6H, m, C₆H₅CH₂O, C6-H),
8.02(2H, d, J=9.0Hz, C2'-H, C6'-H),
8.27(1H, dd, J=7.6Hz, 1.9Hz, C5-H/C7-H),
8.39(1H, dd, J=7.9Hz, 1.9Hz, C5-H/C7-H).

EXAMPLE 9

Synthesis of 8-ethoxycarbonyl-4'-[(2-quinolinyl)methoxy]flavone

4'-Hydroxy-8-ethoxycarbonylflavone (1 eq.) and 2-chloromethylquinoline (1.1 eq.) were dissolved in DMF, followed by the addition of potassium carbonate (1.2 eq.). The resulting mixture was stirred at 100° C. and, subsequent to the completion of the reaction, was charged into water. The water layer was extracted with ethyl acetate. The organic layer was washed with water and a saturated aqueous solution of sodium chloride, dried over anhydrous sodium sulfate, and then concentrated under reduced pressure. The residue was recrystallized from DMF-ethanol, whereby the title compound represented by the following formula was obtained (yield: 64%).

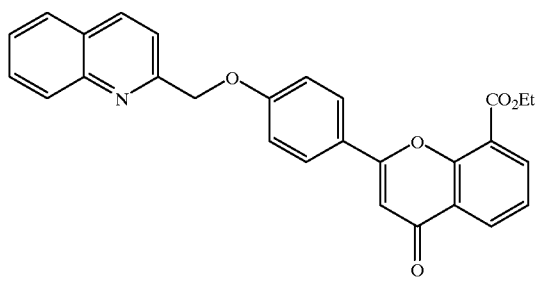

m.p.: 165.1–166.3° C.

¹H-NMR(CDCl₃); δ1.44(3H, t, J=7.1Hz, CO₂CH₂CH₃),
4.47(2H, q, J=7.1Hz, CO₂CH₂CH₃),
5.46(2H, s, C₉H₆NCH₂O), 6.77(1H, s, C3-H),
7.15(2H, d, J=9.0Hz, C3'-H, C5'-H),
7.43(1H, t, J=7.7Hz, C6-H),
7.51–7.59(1H, m, quinoline C6-H),
7.64(1H, d, J=8.5Hz, quinoline C3-H),
7.71–7.77(1H, m, quinoline C7-H),
7.78–7.84(1H, m, quinoline C5-H),
8.02(2H, d, J=9.0Hz, C2'-H, C6'-H),
8.07–8.11(1H, m, quinoline C8-H),
8.20(1H, d, J=8.5Hz, quinoline C4-H),
8.27(1H, dd, J=7.6Hz, 1.8Hz, C5-H/C7-H),
8.40(1H, dd, J=7.8Hz, 1.8Hz, C5-H/C7-H).

EXAMPLE 10

Synthesis of 8-ethoxycarbonyl-4'-[(2-naphthyl)methoxy]flavone

In a similar manner as in Example 9, the title compound represented by the following formula was obtained from 4'-hydroxy-8-ethoxycarbonylflavone and 2-chloromethylnaphthalene (yield: 41%).

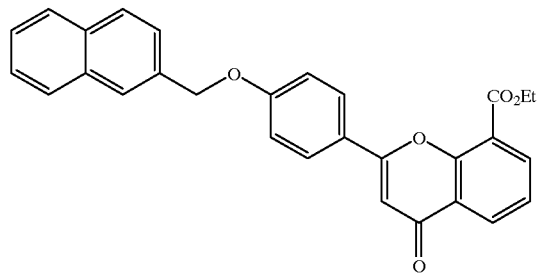

m.p.: 113.2–116.7° C.

EXAMPLE 11

Synthesis of 8-ethoxycarbonyl-4'-[(2-quinazolyl)methoxy]flavone

In a similar manner as in Example 9, the title compound represented by the following formula was obtained from 4'-hydroxy-8-ethoxycarbonylflavone and 2-chloromethylquinazoline (yield: 65%).

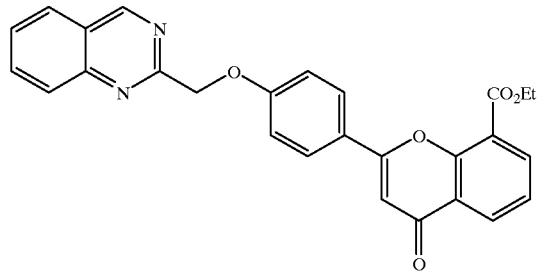

m.p.: 226.3–226.8° C.

¹H-NMR(CDCl₃); δ1.44(3H, t, J=7.1Hz, CO₂CH₂CH₃),
4.47(2H, q, J=7.1Hz, CO₂CH₂CH₃),
5.55(2H, s, C₈H₅N₂—CH₂—O), 6.68(1H, s, C3-H),
7.20(2H, d, J=9.0Hz, C3'-H, C5'-H),
7.42(1H, t, J=7.8Hz, C6-H),
7.69–7.73(1H, m, quinazoline C6-H),
7.95–8.06(3H, m, quinazoline C5-H,
quinazoline C7-H, quinazoline C8-H),
8.02(2H, d, J=9.0Hz, C2'-H, C6'-H),
8.28(1H, dd, J=7.6Hz, 1.8Hz, C5-H/C7-H),
8.39(1H, dd, J=7.9Hz, 1.8Hz, C5-H/C7-H),
9.46(1H, s, quinazoline C4-H).

EXAMPLE 12

Synthesis of 8-ethoxycarbonyl-3'-[(2-quinolinyl)methoxy]flavone

In a similar manner as in Example 9, the title compound represented by the following formula was obtained from 3'-hydroxy-8-ethoxycarbonylflavone and 2-chloromethylquinoline (yield: 13%).

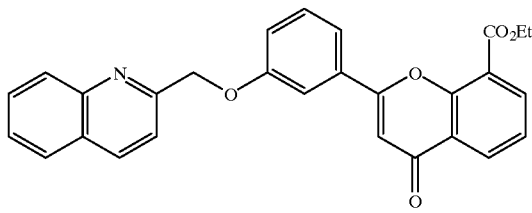

m.p.: 161.4–162.5° C.

| $^1$H-NMR(CDCl$_3$); | δ1.40(3H, t, J=7.1Hz, CO$_2$CH$_2$CH$_3$), 4.42(2H, q, J=7.1Hz, CO$_2$CH$_2$CH$_3$), 5.43(2H, s, C$_9$H$_6$N—CH$_2$—O), 6.82(1H, s, C3-H), 7.14–7.19(1H, m, C4'-H), 7.39–7.43(1H, m, C6-H), 7.54–7.59(1H, m, quinoline C6-H), 7.63(1H, d, J=8.5Hz, quinoline C3-H), 7.73–7.77(1H, m, quinoline C7-H), 7.82–7.85(1H, m, quinoline C5-H), 8.01–8.09(4H, m, quinoline C8-H, C2'-H, C5'-H, C6'-H), 8.21(1H, d, J=8.5Hz, quinoline C3-H), 8.30(1H, m, C5-H/C7-H), 8.41(1H, m, C5-H/C7-H). |
|---|---|

EXAMPLE 13

Synthesis of 6-bromo-8-ethoxycarbonyl-3'-[(2-quinolinyl)methoxy]flavone

In a similar manner as in Example 9, the title compound represented by the following formula was obtained from 6-bromo-3'-hydroxy-8-ethoxycarbonylflavone and 2-chloromethylquinoline (yield: 55%).

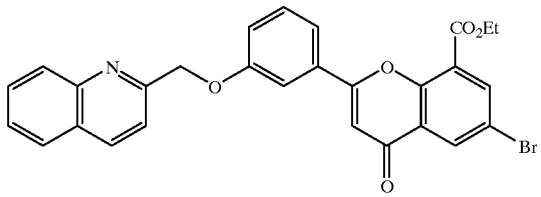

m.p.: 148.8–150.2° C.

| $^1$H-NMR(CDCl$_3$); | δ1.39(3H, t, J=7.1Hz, CO$_2$CH$_2$CH$_3$), 4.41(2H, q, J=7.1Hz, CO$_2$CH$_2$CH$_3$), 5.42(2H, s, C$_9$H$_6$NCH$_2$O), 6.80(1H, s, C3-H), 7.12–7.16(1H, m, C4'-H), 7.37(1H, t, J=8.0Hz, C5'-H), 7.46–7.49(1H, m, quinoline C6-H), 7.60(1H, d, J=8.6Hz, quinoline C3-H), 7.59–7.63(1H, m, quinoline C7-H), 7.65–7.80(3H, m, quinoline C5-H, C2'-H, C6'-H), 8.04(1H, d, J=8.6Hz, quinoline C8-H), 8.15(1H, d, J=8.5Hz, quinoline C4-H), 8.31(1H, d, J=2.6Hz, C5-H/C7-H), 8.45(1H, d, J=2.6Hz, C5-H/C7-H). |
|---|---|

EXAMPLE 14

Synthesis of 6-bromo-8-ethoxycarbonyl-3'-[2-(7-chloroquinolinyl)methoxy]flavone

In a similar manner as in Example 9, the title compound represented by the following formula was obtained from 6-bromo-3'-hydroxy-8-ethoxycarbonylflavone and 7-chloro-2-(chloromethyl)quinoline (yield: 52%).

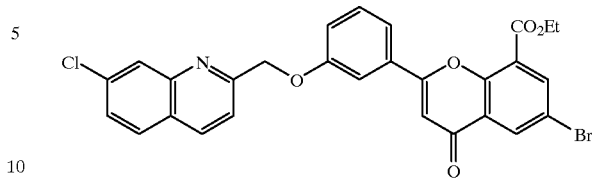

m.p.: 181.6–182.1° C.

| $^1$H-NMR(CDCl$_3$); | δ1.40(3H, t, J=7.1Hz, CO$_2$CH$_2$CH$_3$), 4.40(2H, q, J=7.1Hz, CO$_2$CH$_2$CH$_3$), 5.39(2H, s, C$_9$H$_5$NClCH$_2$O), 6.80(1H, s, C3-H), 7.11–7.14(1H, m, C4'-H), 7.38(1H, t, J=8.0Hz, C5'-H), 7.42–7.47(1H, m, quinoline C6-H), 7.60(2H, d, J=8.4Hz, quinoline C3-H, quinoline C5-H), 7.68–7.72(2H, m, C2'-H, C6'-H), 8.03(1H, s, quinoline C8-H), 8.11(1H, d, J=8.5Hz, quinoline C4-H), 8.31(1H, d, J=2.5Hz, C5-H/C7-H), 8.45(1H, d, J=2.5Hz, C5-H/C7-H). |
|---|---|

EXAMPLE 15

Synthesis of 6-bromo-8-ethoxycarbonyl-3'-[(2-quinazolinyl)methoxy]flavone

In a similar manner as in Example 9, the title compound represented by the following formula was obtained from 6-bromo-3'-hydroxy-8-ethoxycarbonylflavone and 2-chloromethylquinazoline (yield: 47%).

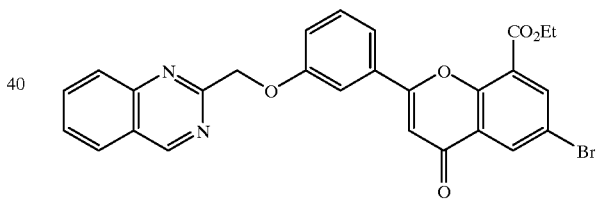

m.p.: 179.7–180.3° C.

| $^1$H-NMR(CDCl$_3$); | δ1.39(3H, t, J=7.1Hz, CO$_2$CH$_2$CH$_3$), 4.40(2H, q, J=7.1Hz, CO$_2$CH$_2$CH$_3$), 5.50(2H, s, C$_8$H$_5$N$_2$CH$_2$O), 6.80(1H, s, C3-H), 7.17–7.21(1H, m, C4'-H), 7.38(1H, t, J=8.0Hz, C5'-H), 7.57–7.65(2H, m, C6'-H, quinazoline C6-H), 7.72–7.73(1H, m, C2'-H), 7.85–7.92(2H, m, quinazoline C5-H, quinazoline C7-H), 8.02(1H, d, J=9.0Hz, quinazoline C8-H), 8.30(1H, d, J=2.6Hz, C5-H/C7-H), 8.45(1H, d, J=2.6Hz, C5-H/C7-H), 9.40(1H, s, quinazoline C4-H). |
|---|---|

EXAMPLE 16

Synthesis of 6-bromo-8-ethoxycarbonyl-3'-[2-naphthylmethoxy]flavone

In a similar manner as in Example 9, the title compound represented by the following formula was obtained from 6-bromo-3'-hydroxy-8-ethoxycarbonylflavone and 2-chloromethylnaphthalene (yield: 70%).

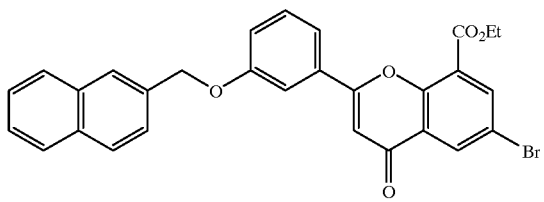

m.p.: 211.4–212.8° C.

| <sup>1</sup>H-NMR(CDCl<sub>3</sub>); | δ1.38(3H, t, J=7.1Hz, CO<sub>2</sub>CH<sub>2</sub>CH<sub>3</sub>),<br>4.41(2H, q, J=7.1Hz, CO<sub>2</sub>CH<sub>3</sub>),<br>5.42(2H, s, C<sub>10</sub>H<sub>7</sub>CH<sub>2</sub>O), 6.80(1H, s, C3-H),<br>7.13–7.19(1H, m, C4'-H), 7.26–7.48(4H, m, Ar-H),<br>7.54–7.59(1H, m, Ar-H), 7.76–7.99(5H, m, Ar-H),<br>8.31(1H, d, J=2.6Hz, C5-H/C7-H),<br>8.45(1H, d, J=2.6Hz, C5-H/C7-H). |
|---|---|

EXAMPLE 17

Synthesis of 6-bromo-8-ethoxycarbonyl-3'-[2-(1-methylbenzimidazolyl)methoxy]flavone In a similar manner as in Example 9, the title compound represented by the following formula was obtained from 6-bromo-3'-hydroxy-8-ethoxycarbonylflavone and 2-chloromethyl-1-methylbenzimidazole (yield: 65%).

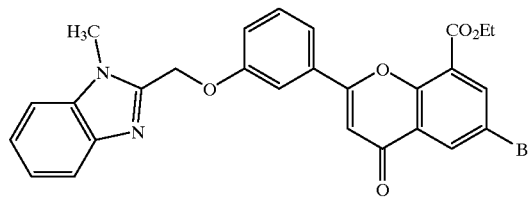

m.p.: 209.3–210.2° C.

| <sup>1</sup>H-NMR(CDCl<sub>3</sub>); | δ1.39(3H, t, J=7.1Hz, CO<sub>2</sub>CH<sub>2</sub>CH<sub>3</sub>),<br>3.86(3H, s, NCH<sub>3</sub>),<br>4.41(2H, q, J=7.1Hz, CO<sub>2</sub>CH<sub>3</sub>),<br>5.42(2H, s, C<sub>8</sub>H<sub>7</sub>N<sub>2</sub>CH<sub>2</sub>O), 6.82(1H, s, C3-H),<br>7.22–7.31(4H, m, benzimidazole C5-H,<br>benzimidazole C6-H, benzimidazole C7-H,<br>C4'-H), 7.39(1H, t, J=8.0Hz, C5'-H),<br>7.60(1H, d, J=7.8Hz, C6'-H),<br>7.72–7.76(1H, m, benzimidazole C4-H, C2'-H),<br>8.31(1H, d, J=2.6Hz, C5-H/C7-H),<br>8.46(1H, d, J=2.6Hz, C5-H/C7-H). |
|---|---|

EXAMPLE 18

Synthesis of 6-bromo-8-ethoxycarbonyl-3'-[(2-benzothiazolinyl)methoxy]flavone

In a similar manner as in Example 9, the title compound represented by the following formula was obtained from 6-bromo-3'-hydroxy-8-ethoxycarbonylflavone and 2-chloromethylbenzothiazole (yield: 35%).

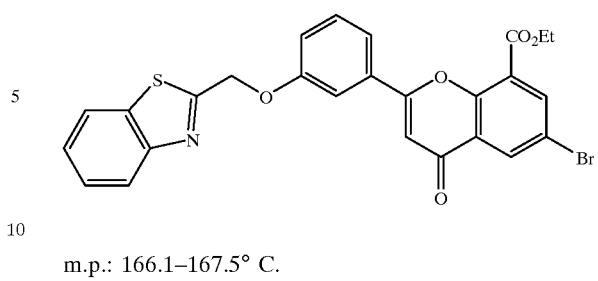

m.p.: 166.1–167.5° C.

| <sup>1</sup>H-NMR(CDCl<sub>3</sub>); | δ1.38(3H, t, J=7.1Hz, CO<sub>2</sub>CH<sub>2</sub>CH<sub>3</sub>),<br>4.41(2H, q, J=7.1Hz, CO<sub>2</sub>CH<sub>2</sub>CH<sub>3</sub>),<br>5.42(2H, s, C<sub>7</sub>H<sub>4</sub>NSCH<sub>2</sub>O), 6.80(1H, s, C5-H),<br>8.31(1H, d, J=2.6Hz, C5-H/C7-H),<br>8.45(1H, d, J=2.6Hz, C5-H/C7-H). |
|---|---|

EXAMPLE 19

Synthesis of 8-carboxy-4'-(2-quinolinylmethoxy)flavone

8-Ethoxycarbonyl-4'-(2-quinolinylmethoxy)flavone was dissolved in a mixed solvent of methanol:THF:5% aqueous solution of lithium hydroxide (1:1:1 V/V), followed by stirring at room temperature for 2 days. The reaction mixture was acidified with 3 N hydrochloric acid. The resulting precipitate was collected by filtration, washed with water and methanol, and then recrystallized from DMF, whereby the title compound represented by the following formula was obtained (yield: 89%).

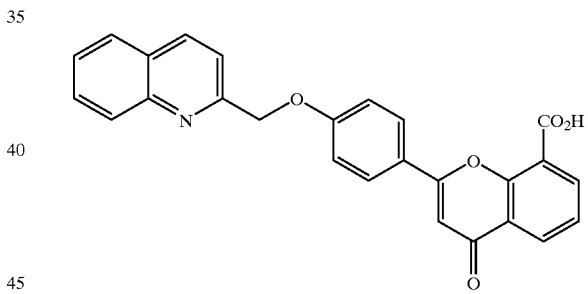

m.p.: 223.4–225.9° C.

| <sup>1</sup>H-NMR(DMSO-d<sub>6</sub>); | δ5.50(2H, s, C<sub>9</sub>H<sub>6</sub>NCH<sub>2</sub>O), 6.97(1H, s, C3-H),<br>7.27(2H, d, J=8.7Hz, C3'-H, C5'-H),<br>7.52–7.56(1H, m, C6-H),<br>7.60–7.64(1H, m, quinoline C6-H),<br>7.69(1H, d, J=8.4Hz, quinoline C3-H),<br>7.77–7.81(1H, m, quinoline C7-H),<br>7.98(1H, d, J=7.9Hz, quinoline C5-H),<br>8.03(1H, d, J=8.4Hz, quinoline C8-H),<br>8.16(2H, d, J=8.7Hz, C2'-H, C6'-H),<br>8.23–8.25(2H, m, C5-H, C7-H),<br>8.41(1H, d, J=8.4Hz, quinoline C4-H). |
|---|---|

EXAMPLE 20

Synthesis of 8-carboxy-4'-(2-naphthylmethoxy)flavone

In a similar manner as in Example 19, the title compound represented by the following formula was obtained from 8-ethoxycarbonyl-4'-(2-naphthylmethoxy)flavone (yield: 43%).

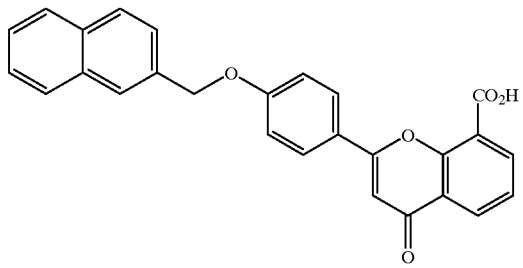

m.p.: 245.1–248.7° C.

¹H-NMR(DMSO-d₆); δ5.43(2H, s, C₁₀H₇CH₂O), 7.09(1H, s, C3-H),
7.28(2H, d, J=8.7Hz, C3'-H, C5'-H),
7.57–7.65(3H, m, C6-H, naphthyl H),
7.97–8.04(4H, m, naphthyl H),
8.20–8.25(4H, m, C5-H, C7-H, C2'-H, C6'-H),
13.59(1H, br.s, ArCO₂H).

EXAMPLE 21

Synthesis of 8-carboxy-4'-(2-quinazolinylmethoxy) flavone

In a similar manner as in Example 19, the title compound represented by the following formula was obtained from 8-ethoxycarbonyl-4'-(2-quinazolinylmethoxy)flavone (yield: 58%).

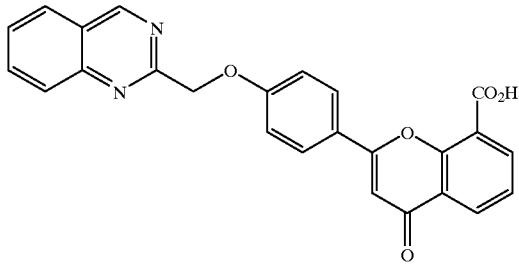

m.p.: 264.8–266.0° C.

¹H-NMR(DMSO-d₆); δ5.59(2H, s, C₈H₅N₂CH₂O), 7.07(1H, s, C3-H),
7.25(2H, d, J=8.8Hz, C3'-H, C5'-H),
7.56(1H, t, J=7.8Hz, C6-H),
7.80–7.84(1H, m, quinazoline C6-H),
8.17–8.19(2H, m, quinazoline C5-H, quinazoline C7-H),
8.21–8.28(5H, m, C5-H, C7-H, C2'-H, C6'-H, quinazoline C8-H),
9.69(1H, s, quinazoline C4-H), 13.51(1H, br.s, CO₂H).

EXAMPLE 22

Synthesis of 8-carboxy-3'-(2-quinolinylmethoxy) flavone

In a similar manner as in Example 19, the title compound represented by the following formula was obtained from 8-ethoxycarbonyl-3'-(2-quinolinylmethoxy)flavone (yield: 40%).

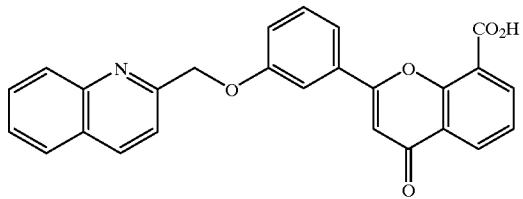

m.p.: >300° C.

¹H-NMR (DMSO-d₆) ; δ5.48 (2H, s, C₉H₆NCH₂O), 7.23 (1H, s, C3-H),
7.31 (1H, dd, J = 8.2 Hz, 2.3 Hz, C4'-H),
7.51 (1H, t, J = 8.0 Hz, C5'-H),
7.58 (1H, t, J = 7.7 Hz, C6-H),
7.61–7.65 (1H, m, quinoline C6-H),
7.75 (1H, d, J = 8.5 Hz, quinoline C3-H),
7.78–7.81 (1H, m, quinoline C7-H),
7.84–7.85 (1H, m, C6'-H),
8.00–8.05 (3H, m, C2'-H, quinoline C5-H, quinoline C8-H),
8.27 (1H, dd, J = 7.9 Hz, 1.8 Hz, C5-H/C7-H),
8.30 (1H, dd, J = 7.6 Hz, 1.8 Hz, C5-H/C7-H),
8.45 (1H, d, J = 8.5 Hz, quinoline C4-H).

EXAMPLE 23

Synthesis of 6-bromo-8-carboxy-3'-(2-guinolinylmethoxy)flavone

In a similar manner as in Example 19, the title compound represented by the following formula was obtained from 6-bromo-8-ethoxycarbonyl-3'-(2-quinolinylmethoxy) flavone (yield: 75%).

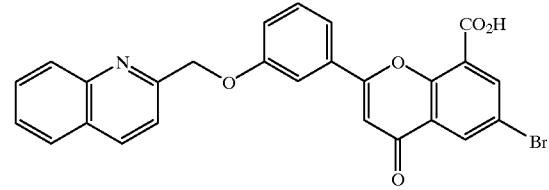

m.p.: 241.6–242.0° C.

¹H-NMR(DMSO-d₆) ; δ5.47 (2H, s, C₉H₆NCH₂O), 7.27 (1H, s, C3-H),
7.30–7.32 (1H, m, C4'-H),
7.50 (1H, t, J = 8.0 Hz, C5'-H),
7.61–7.65 (1H, m, quinoline C6-H),
7.75 (1H, d, J = 8.5 Hz, quinoline C3-H),
7.78–7.83 (2H, m, C6'-H, quinoline C7-H),
7.99–8.05 (3H, m, C2'-H, quinoline C5-H, quinoline C8-H),
8.29 (1H, br.s, CS-H/C7-H),
8.34 (1H, br.s, C5-H/C7-H),
8.45 (1H, d, J = 8.3 Hz, quinoline C4-H).

EXAMPLE 24

Synthesis of 6-bromo-8-carboxy-3'-[2-(7-chloro quinolinyl)methoxy]flavone

In a similar manner as in Example 19, the title compound represented by the following formula was obtained from 6-bromo-8-ethoxycarbonyl-3'-[2-(7-chloro quinolinyl) methoxy]flavone (yield: 68%).

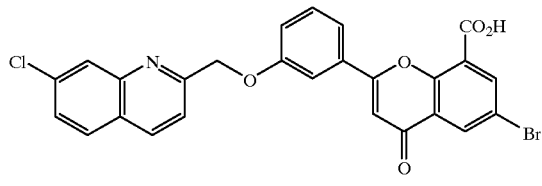

m.p.: 269.0–269.1° C.

¹H-NMR(DMSO-d₆); δ5.47 (2H, s, C₉H₅NClCH₂O),
7.27 (1H, s, C3-H),
7.30 (1H, dd, J = 8.4 Hz, 2.0 Hz, C4'-H),
7.51 (1H, t, J = 8.0 Hz, C5'-H),
7.55 (1H, dd, J = 8.7 Hz, 1.7 Hz, quinoline C6-H),
7.76 (1H, d, J = 8.5 Hz, quinoline C3-H),
7.83 (1H, d, J = 7.7 Hz, C6'-H),
7.99 (1H, s, C2'-H),
8.05–8.07 (2H, m, quinoline C5-H, quinoline C8-H),
8.28 (1H, d, J = 2.4 Hz, C5-H/C7-H)
8.33 (1H, d, J = 2.4 Hz, C5-H/C7-H),
8.48 (1H, d, J = 8.5 Hz, quinoline C4-H).

EXAMPLE 25

Synthesis of 6-bromo-8-carboxy-3'-(2-quinazolinylmethoxy)flavone

In a similar manner as in Example 19, the title compound represented by the following formula was obtained from 6-bromo-8-ethoxycarbonyl-3'-(2-quinazolinylmethoxy) flavone (yield: 41%).

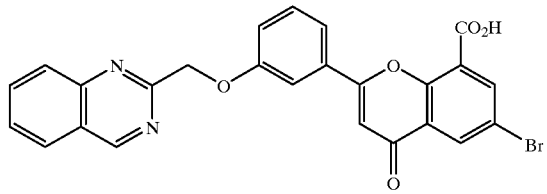

m.p.: 245.7–245.9° C.

¹H-NMR(DMSO-d₆); δ5.54 (2H, s, C₈H₅N₂CH₂O),
7.16 (1H, s, C3-H),
7.28 (1H, dd, J = 8.0 Hz, 1.7 Hz, C4'-H),
7.48 (1H, t, J = 8.0 Hz, C5'-H),
7.76–7.79 (2H, m, C6'-H, quinazoline C6-H),
7.93 (1H, s, C2'-H),
8.02–8.04 (2H, m, quinazoline C5-H, quinazoline C7-H),
8.17 (1H, d, J = 8.0 Hz, quinazoline C8-H),
8.29 (1H, d, J = 2.4 Hz, C5-H/C7-H),
8.31 (1H, d, J = 2.4 Hz, C5-H/C7-H),
9.65 (1H, quinazoline C4-H).

EXAMPLE 26

Synthesis of 6-bromo-8-carboxy-3'-(2-naphthylmethoxy)flavone

In a similar manner as in Example 19, the title compound represented by the following formula was obtained from 6-bromo-8-ethoxycarbonyl-3'-(2-naphthylmethoxy)flavone (yield: 70%).

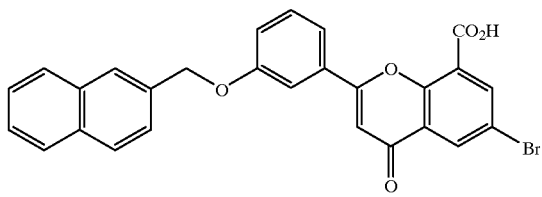

m.p.: 211.4–212.8° C.

¹H-NMR(DMSO-d₆); δ5.34 (2H, s, C₁₀H₇—CH₂—O),
7.23 (1H, s, C3-H),
7.24–7.28 (1H, m, C4'-H), 7.45–7.70 (4H, m, Ar-H),
8.05 (1H, d, J = 8.5 Hz, quinoline CA-H),
8.29 (1H, d, J = 1.8 Hz, C5-H/C7-H),
8.32 (1H, d, J = 1.8 Hz, C5-H/C7-H).

EXAMPLE 27

Synthesis of 6-bromo-8-carboxy-3'-(2-benzothiazolylmethoxy)flavone

In a similar manner as in Example 19, the title compound represented by the following formula was obtained from 6-bromo-8-ethoxycarbonyl-3'-(2-benzothiazolylmethoxy) flavone (yield: 52%).

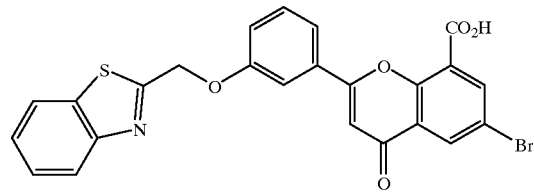

m.p.: 250.2–251.4° C.

¹H-NMR(DMSO-d₆); δ5.70 (2H, s, C₇H₄NSCH₂O), 7.22 (1H, s, C3-H),
7.34–7.36 (1H, m, C4'-H), 7.44–7.48 (1H, m, C5-H),
7.52–7.56 (2H, m, benzothiazole C5-H, benzothiazole C6-H),
7.84 (1H, d, J = 7.9 Hz, C6'-H), 7.98 (1H, s, C2'-H),
8.00–8.04 (1H, m, benzothiazole C4-H),
8.10–8.12 (1H, m, benzothiazole C7-H),
8.31 (1H, d, J = 2.5 Hz, C5-H/C7-H),
8.33 (1H, d, J = 2.5 Hz, C5-H/C7-H).

EXAMPLE 28

Synthesis of 6-bromo-8-carboxy-3'-[2-(1-methyl benzimidazolyl)methoxy]flavone

In a similar manner as in Example 19, the title compound represented by the following formula was obtained from 6-bromo-8-ethoxycarbonyl-3'-[2-(1-methyl benzimidazolyl) methoxy]flavone (yield: 82%).

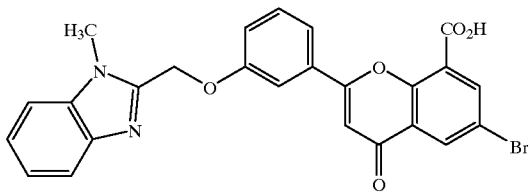

m.p.: 287.4–288.5° C.

¹H-NMR(DMSO-d₆); δ4.01 (3H, s, NCH₃), 5.71 (2H, s,
C₈H₇NCH₂O), 7.23 (1H, s, C3-H),
7.41–7.50 (3H, m, C4'-H, benzimidazole C5-H,
benzimidazole C6-H),
7.56 (1H, t, J = 8.0 Hz, C5'-H),
7.77–7.81 (1H, m, benzimidazole C4-H,
benzimidazole C7-H),
7.87 (1H, d, J = 7.7 Hz, C6'-H),
8.00 (1H, s, C2'-H),
8.31 (1H, d, J = 2.1 Hz, C5-H/C7-H),
8.46 (1H, d, J = 2.1 Hz, C5-H/C7-H).

EXAMPLE 29

Synthesis of 8-carboxy-3-hydroxy-4'-[(2-quinolinyl)methoxy]flavone 1) 4-(2-Quinolinyl)benzaldehyde (5 mmol) and 3-carboxy-2-hydroxyacetophenone (5 mmol) were dissolved in 50 ml of ethanol, followed by the addition of 30 ml of a 25% aqueous solution of potassium hydroxide. After the resultant mixture was stirred at room temperature for 1 week, the reaction mixture was charged in ice water and 3 N hydrochloric acid was added for acidification. The resulting precipitate was collected by filtration, washed with water and then dried in air. It was then recrystallized from DMF-ethanol, whereby 3'-carboxy-2'-hydroxy-4-(2-quinolinylmethoxy)chalcone was obtained (yield: 38%).

m.p.: 232.9–235.3° C.

¹H-NMR(DMSO-d₆); δ5.44 (2H, s, C₉H₆NCH₂O), 6.78 (1H, t,
C5'-H),
7.14 (2H, d, J = 8.6 Hz, C3-H, C5-H),
7.57 (1H, d, J = 15.8 Hz, Hα),
7.60–7.64 (1H, m, quinoline C6-H),
7.67–7.81 (5H, m, quinoline C7-H, quinoline
C3-H, C2-H, C6-H, C4'-H/C6'-H),
7.73 (1H, d, J = 15.8 Hz, Hβ),
7.93–7.95 (1H, m, C4'-H/C6'-H),
7.99 (1H, d, J = 8.2 Hz, quinoline C5-H),
8.03 (1H, d, J = 8.5 Hz, quinoline C8-H),
8.42 (1H, d, J = 8.5 Hz, quinoline C4-H).

2) 3'-Carboxy-2'-hydroxy-4-[(2-quinolinyl)methoxy]chalcone (1.2 mmol) was dissolved in 35 ml of methanol, followed by the addition of 2 ml of 16% potassium hydroxide. While the resulting mixture was stirred over an ice bath, 2.0 ml of a 15% aqueous solution of hydrogen peroxide were gradually added dropwise. The resulting mixture was allowed to stand for 24 hours at 4° C. The reaction mixture was acidified with 1 N hydrochloric acid. The resulting precipitate was collected by filtration and the recrystallized from DMF, whereby the title compound represented by the following formula was obtained (yield: 49%).

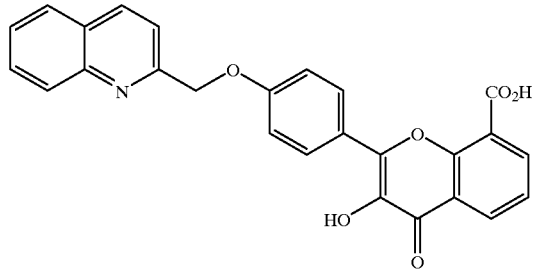

m.p.: 226.5–227.8° C.

¹H-NMR(DMSO-d₆); δ5.47 (2H, s, C₉H₆NCH₂O),
7.24 (2H, d, J = 9.0 Hz, C3'-H, C5'-H),
7.30 (1H, t, J = 7.6 Hz, C6-H),
7.61–7.64 (1H, m, quinoline C6-H),
7.72 (1H, d, J = 8.5 Hz, quinoline C3-H),
7.78–7.82 (2H, m, quinoline C7-H, C5-H/
C7-H),
7.94 (1H, dd, J = 7.9 Hz, 1.6 Hz, C5-H/C7-H),
8.01 (1H, d, J = 8.4 Hz, quinoline C5-H),
8.05 (1H, d, J = 8.5 Hz, quinoline C8-H),
8.44 (1H, d, J = 8.5 Hz, quinoline C4-H),
8.44 (2H, d, J = 9.0 Hz, C2'-H, C6'-H).

EXAMPLE 30

Synthesis of 3-[2-(phthalimido)ethoxy]-8-[2-(phthalimido)ethoxycarbonyl]4'-[(2-quinolinyl)methoxy]flavone DMF (20 ml) was added to a mixture of 2.50 g (5.7 mmol) of 8-carboxy-3-hydroxy-4'-[(2-quinolinyl)methoxy]flavone, 3.18 g (12.5 mmol) of 2-bromoethylphthalimide and 1.73 g (12.5 mmol) of potassium carbonate, followed by overnight stirring at 70° C. The reaction mixture was charged into water. The resulting precipitate was collected by filtration and then recrystallized from ethanol, whereby 2.85 g of the title compound represented by the following formula were obtained as a white solid (yield: 62%).

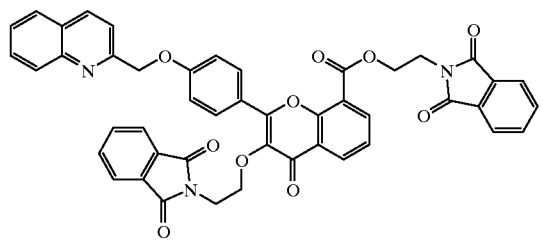

m.p.: 211.2–212.4° C.

¹H-NMR(CDCl₃); δ3.95–4.04 (2H, m, NCH₂CH₂O),
4.05–4.12 (2H, m, NCH₂CH₂O),

-continued 4.42–4.49 (2H, m, NCH₂CH₂O),
4.56–4.62 (2H, m, NCH₂CH₂O),
5.24 (2H, s, C₉H₆NCH₂O),
6.74 (2H, d, J = 9.0 Hz, C3'-H, C5'-H),
7.37 (1H, t, J = 7.8 Hz, C6-H),
7.55–7.86 (12H, m, 8H of phthalimide, quinoline
  C3-H, quinoline C5-H, quinoline C6-H,
  quinoline C7-H),
8.04 (2H, d, J = 9.0 Hz, C2'-H, C6'-H),
8.09–8.13 (1H, m, quinoline C8-H),
8.20–8.26 (2H, m, C5-H, C7-H),
8.35 (1H, d, J = 7.9 Hz, quinoline C4-H).

EXAMPLE 31

Synthesis of 8-carboxy-3-(2-phthalimido)ethoxy-4'-
[(2-quinolinyl)methoxy]flavone 3-[2-(Phthalimido)ethoxy]-8-[2-(phthalimido)
ethoxycarbonyl]4'-[(2-quinolinyl)methoxy]flavone was subjected to alkaline hydrolysis by a method known per se in the art, whereby the title compound represented by the following formula was obtained (yield: 89%).

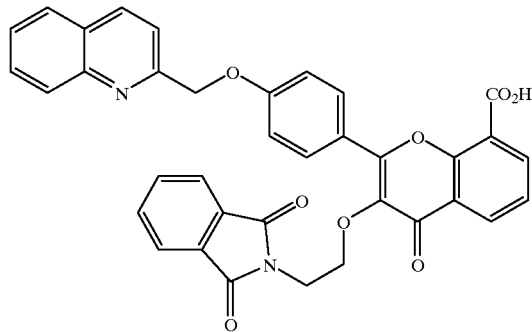

m.p.: 170.2–173.3° C.

¹H-NMR(DMSO-d₆) ; δ3.45–3.55 (2H, m, NCH₂CH₂O),
4.18–4.19 (2H, m, NCH₂CH₂O),
5.44 (2H, s, C₉H₆NCH₂O),
7.20 (2H, d, J = 8.6 Hz, C3'-H, C5'-H),
7.48–7.55 (3H, m, C6-H, phthalimide C5-H,
  phthalimide C6-H),
7.61–7.65 (1H, m, quinoline C6-H),
7.68–7.70 (2H, m, phthalimide C4-H,
  phthalimide C7-H),
7.80 (1H, d, J = 8.5 Hz, quinoline C3-H),
7.78–7.82 (1H, m, quinoline C7-H),
7.99–8.05 (2H, m, quinoline C5-H,
  quinoline C8-H),
8.22–8.27 (2H, m, C5-H, C7-H),
8.35 (2H, J = 8.6 Hz, C2'-H, C6'-H),
8.43 (1H, d, J = 8.5 Hz, quinoline C4-H).

EXAMPLE 32

Synthesis of 8-carboxy-3-[2-(N,N-dimethylamino)
ethoxy]-4'-[(2-quinolinyl)methoxy]flavone
hydrochloride 8-Carboxy-3-(2-phthalimido)ethoxy-4'-[(2-quinolinyl)
methoxy]flavone (0.18 g, 0.29 mmol) was suspended in 60 ml of ethanol, followed by the addition of 10 μl of hydrazine. The resulting mixture was refluxed for 1 hour and the resulting precipitate was collected by filtration. Seventy milligrams of the crude amine were suspended in 0.5 ml of 37% formaldehyde, to which 10 mg of cyanosodium borohydride were added. The resulting mixture was stirred overnight at room temperature. After the reaction mixture was concentrated under reduced pressure, the residue was dissolved in ethanol and several droplets of 1 N hydrochloric acid were added, whereby 35 mg of the title compound represented by the following formula were obtained (yield: 21%).

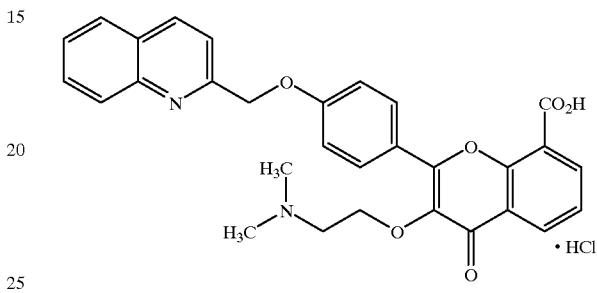

m.p.: <300° C.

¹H-NMR(DMSO-d₆) ; δ2.92 (3H, s, NCH₃), 2.96 (3H, s, NCH₃),
3.48–3.53 (2H, m, NCH₂CH₂O),
4.28–4.36 (2H, m, NCH₂CH₂O),
5.36 (2H, s, C₉H₆NCH₂O),
7.31 (2H, d, J = 9.0 Hz, C3'-H, C5'-H),
7.57 (1H, t, J = 7.7 Hz, C6-H),
7.68–7.75 (1H, m, quinoline C6-H),
7.83–7.93 (2H, m, quinoline C3-H,
  quinoline C7-H),
8.16 (2H, d, J = 9.3 Hz, quinoline C8-H),
8.28–8.35 (5H, m, C5-H, C7-H, C2'-H,
  C6'-H, HCl),
8.66 (1H, d, J = 8.5 Hz, quinoline C4-H),
10.99 (1H, br.s, ArCO₂H).

EXAMPLE 33

Synthesis of 8-benzenesulfonylamidocarbonyl-6-
bromo-4'-(2-quinolinylmethoxy)flavone 6-Bromo-8-carboxy-4'-[(2-quinolinyl)methoxy]flavone (0.50 g, 1.0 mmol), benzenesulfonamide (0.19 g, 1.2 mmol) and DMAP (0.15 g, 1.2 mmol) were dissolved in 10 ml of DMF, followed by the addition of 0.23 g (1.2 mmol) of water-soluble carbodiimide. The resulting mixture was stirred overnight at room temperature and the reaction mixture was charged in water. The water layer was extracted with ethyl acetate. The organic layer was washed with 1 N hydrochloric acid and a saturated aqueous solution of sodium chloride, dried over anhydrous sodium sulfate, and then concentrated under reduced pressure. The residue was recrystallized from DMF-EtOH, whereby the title compound represented by the following formula was obtained (yield: 16%).

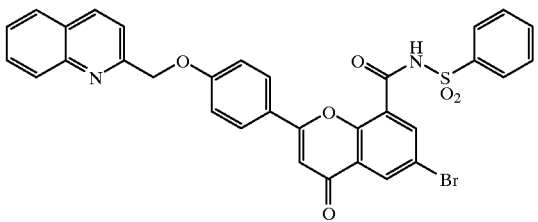

m.p.: 255.6–256.5° C.

¹H-NMR(DMSO-d₆) ; δ5.56 (2H, s, C₉H₆NCH₂O), 7.06 (1H, s, C3-H),
7.18 (2H, d, J = 8.9 Hz, C3'-H, C5'-H),
7.62–7.69 (4H, m, phenyl C3-H, phenyl C4-H,
phenyl C5-H, quinoline C6-H),
7.72 (1H, d, J = 8.6 Hz, quinoline C3-H),
7.79–7.83 (1H, m, quinoline C7-H),
7.87 (2H, d, J = 8.9 Hz, C2'-H, C6'-H),
8.02 (1H, d, J = 8.1 Hz, quinoline C5-H),
8.05–8.07 (3H, m, quinoline C8-H,
phenyl C2-H, phenyl C6-H),
8.13 (H, d, J = 2.4 Hz, C5-H/C7-H),
8.21 (1H, d, J = 2.4 Hz, C5-H/C7-H),
8.46 (1H, d, J = 8.6 Hz, quinoline C4-H).

EXAMPLE 34

Synthesis of 6-carboxy-4'-[2-(2-quinolinyl)ethenyl]flavone 1) 4-[2-(2-Quinolinyl)ethenyl]benzaldehyde (5 mmol) and 5-carboxy-2-hydroxyacetophenone (5 mmol) were dissolved in 50 ml of ethanol, followed by the addition of 30 ml of a 25% aqueous solution of potassium hydroxide. After the resulting mixture was stirred at room temperature for 1 week, the reaction mixture was charged into ice water, to which 3 N hydrochloric acid was added for acidification. The resulting precipitate was collected by filtration, washed with water, dried in air and then recrystallized form DMF-ethanol, whereby 5'-carboxy-2'-hydroxy-4-[(2-quinolinyl)methoxy]chalcone was obtained (yield: 26%).

m.p.: 257.7–260.0° C.

¹H-NMR(DMSO-d₆) ; δ7.11 (1H, d, C3'-H),
7.56–7.64 (2H, m, quinoline C6-H, Hα),
7.75–7.79 (1H, m, quinoline C7-H),
7.80–7.84 (3H, m, C₉H₆NCH=CHC₆H₄—,
quinoline C3-H),
7.89–8.99 (6H, m, C2-H, C3-H, C5-H, C6-H,
quinoline C5-H, Hβ),
8.06 (1H, dd, J = 8.6 Hz, 2.1 Hz, C4'-H),
8.39 (1H, d, J = 8.6 Hz, quinoline C4-H),
8.57 (1H, d, J = 2.1 Hz, C6'-H), 12.61 (1H,
s, OH),
12.93 (1H, br.s, COOH).

2) 5'-Carboxy-2'-hydroxy-4-[2-(2-quinolinyl)ethenyl]chalcone (1 eq.) and selenium dioxide (2.2 eq.) were refluxed for 8 hours in dioxane. The reaction mixture was allowed to cool down to room temperature. The resulting crystals were collected by filtration. The thus-obtained crude crystals were recrystallized form DMF, whereby the title compound represented by the following formula was obtained (yield: 28%).

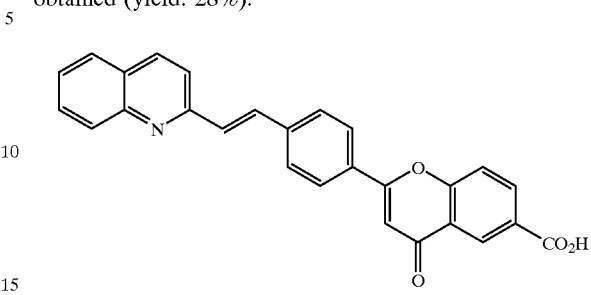

m.p.: >300° C.

¹H-NMR(DMSO-d₆) ; δ7.10 (1H, s, C3-H), 7.55–7.59
(1H, m, quinoline C6-H),
7.64 (1H, d, J = 16.4 Hz,
C₉H₆NCH=CHC₆H₄—),
7.74–7.78 (1H, m, quinoline C7-H),
7.86 (1H, d, J = 8.7 Hz, C8-H),
7.89 (1H, d, J = 8.5 Hz, quinoline C3-H),
7.90 (1H, d, J = 16.4 Hz,
C₉H₆NCH=CHC₆H₄—),
7.90–7.93 (1H, m, quinoline C5-H),
7.93 (2H, d, J = 8.6 Hz, C3'-H, C5'-H),
8.01 (1H, d, J = 8.5 Hz, quinoline C8-H),
8.17 (2H, d, J = 8.6 Hz, C2'-H, C6'-H),
8.32 (1H, dd, J = 8.7 Hz, C7-H),
8.36 (1H, d, J = 8.5 Hz, quinoline C4-H),
8.60 (1H, d, J = 2.1 Hz, C5-H).

EXAMPLE 35

Synthesis of 6-carboxy-3'-[2-(2-quinolinyl)ethenyl]flavone

In a similar manner as in Example 34, the title compound represented by the following formula was obtained from 3-[2-(2-quinolinyl)ethenyl]benzaldehyde and 5-carboxy-2-hydroxyacetophenone (yield: 5%).

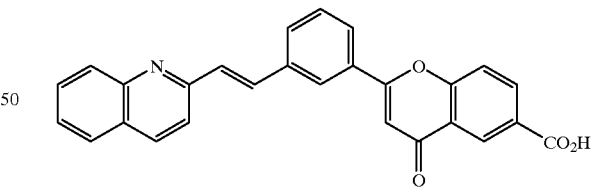

m.p.: 275–277° C.

¹H-NMR(DMSO-d₆) ; δ7.21 (1H, s, C3-H),
7.56–7.60 (1H, m, quinoline C6-H),
7.64–7.68 (1H, m, C5'-H),
7.67 (1H, d, J = 7 8 Hz, C8-H),
7.70 (1H, d, J = 16.5 Hz, olefin-H),
7.75–7.79 (1H, m, quinoline C7-H),
7.88 (1H, d, J = 8.3 Hz, quinoline C3-H),
7.93–7.98 (3H, m, C4'-H, C6'-H, olefin-H),
8.02 (1H, d, J = 8.5 Hz, quinoline C5-H), -continued 8.08 (1H, d, J = 7.7 Hz, quinoline C8-H),
8.33–8.35 (1H, m, C7-H),
8.37 (1H, d, J = 8.7 Hz, quinoline C4-H),
8.49 (1H, br.s, C2'-H), 8.64 (1H, br.s, C5-H).

EXAMPLE 36

Synthesis of 6-cyano-3'-[2-(2-quinolinyl)ethenyl]-flavone

In a similar manner as in Example 35, the title copound represented by the following formula was obtained from 3-[2-(2-quinolinyl)ethenyl]benzaldehyde and 5-cyano-2-hydroxyacetophenone (yield: 39%).

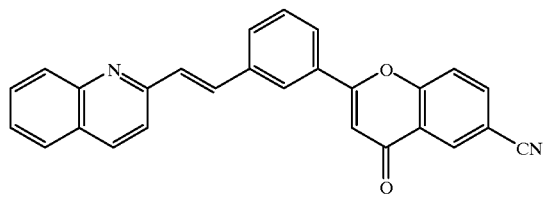

m.p.: 271.8–272.9° C.

$^1$H-NMR(DMSO-d$_6$) ; δ7.24 (1H, s, C3-H),
7.56–7.60(1H, m, quinoline C6-H),
7.65 (1H, t, J = 7.8 Hz, C5'-H),
7.68 (1H, d, J = 16.3 Hz, olefin-H),
7.75–7.79 (1H, m, quinoline C7-H),
7.87 (1H, d, J = 8.6 Hz, quinoline C3-H),
7.92 (1H, d, J = 16.3 Hz, olefin-H),
7.94–7.96 (2H, m, C4-H, C6-H),
8.01 (1H, d, J = 8.3 Hz, quinoline C5-H),
8.03 (1H, d, J = 8.7 Hz, C8-H),
8.06 (1H, d, J = 7.9 Hz, quinoline C8-H),
8.21 (1H, dd, J = 8.7 Hz, 1.9 Hz, C7-H),
8.38 (1H, d, J = 8.6 Hz, quinoline C4-H),
8.42 (1H, d, J = 1.9 Hz, C5-H),
8.46 (1H, s, C2'-H).

EXAMPLE 37

Synthesis of 3'-[2-(2-quinolinyl)ethenyl]-6-(5-tetrazolyl)flavone

In a similar manner as in Example 34, the title copound represented by the following formula was obtained from 3-[2-(2-quinolinyl)ethenyl]benzaldehyde and 2-hydroxy-5-(5-tetrazolyl)acetophenone (yield: 10%).

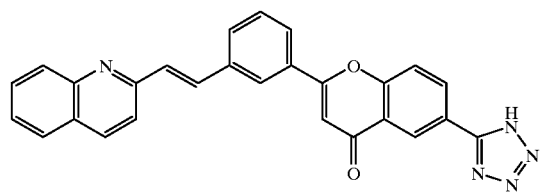

m.p.: >300° C.

$^1$H-NMR(DMSO-d$_6$) ; δ7.20 (1H, s, C3-H),
7.66–7.71 (2H, m, C5'-H, quinoline C6-H),
7.80 (1H, d, J = 16.2 Hz, olefin-H),
7.86–7.90 (1H, m, quinoline C7-H),
7.96 (1H, d, J = 8.0 Hz, quinoline C3-H),
8.05–8.18 (6H, m, olefin-H, C4'-H,
C6'-H, C8-H, quinoline C5-H,
quinoline C8-H),
8.48 (1H, s, C2'-H),
8.48–8.51 (1H, m, quinoline C4-H),
8.60 (1H, d, J = 8.0 Hz, C7-H),
8.76 (1H, s, C5-H).

EXAMPLE 38

Synthesis of 8-carboxy-4'-[2-(2-quinolinyl)ethenyl]flavone

In a similar manner as in Example 34, the title compound represented by the following formula was obtained from 4-[2-(2-quinolinyl)ethenyl]benzaldehyde and 3-carboxy-2-hydroxyacetophenone (yield: 44%).

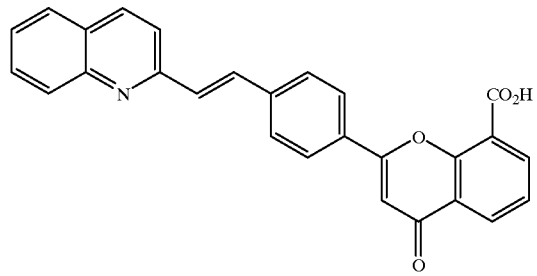

m.p.: 268.1–270.0° C.

$^1$H-NMR(DMSO-d$_6$) ; δ7.16 (1H, s, C3-H),
7.57 (2H, t, J = 7.6 Hz, C6-H, quinoline C6-H),
7.65 (1H, d, J = 16.4 Hz, olefin-H),
7.76 (1H, ddd, J = 8.3 Hz, 6.9 Hz,
1.3 Hz, quinoline C7-H),
7.88 (1H, d, J = 8.5 Hz, quinoline C3-H),
7.90 (1H, d, J = 16.4 Hz, olefin-H),
7.92–7.96 (3H, n, C2'-H,
C6'-H, quinoline C5-H),
8.01 (1H, d, J = 8.3 Hz, quinoline C8-H),
8.25–8.29 (4H, m, J = 8.6 Hz,
C5-H, C3'-H, C5'-H),
8.36 (1H, d, J = 8.5 Hz, quinoline C4-H).

EXAMPLE 39

Synthesis of 8-carboxy-3'-[2-(2-quinolinyl)ethenyl]flavone

In a similar manner as in Example 34, the title copound represented by the following formula was obtained from 3-[2-(2-quinolinyl)ethenyl]benzaldehyde and 3-carboxy-2-hydroxyacetophenone (yield: 52%).

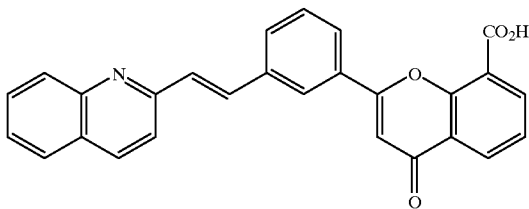

m.p.: >300° C.

$^1$H-NMR(DMSO-$d_6$) ; δ7.20 (1H, s, C3-H),
7.59 (1H, t, J = 7.7 Hz, C6-H),
7.62–7.66 (1H, m, quinoline C6-H),
7.67 (1H, t, J = 7.7 Hz, C5'-H),
7.70 (1H, d, J = 16.3 Hz, C$_9$H$_6$NCH=CHC$_6$H$_4$—),
7.81–7.86 (1H, m, quinoline C7-H),
7.95 (1H, d, J = 7.7 Hz, C4'-H/C6'-H),
7.97–8.00 (1H, m, C4'-H/C6'-H),
7.98 (1H, d, J = 8.6 Hz, quinoline C3-H),
8.00 (1H, d, J = 16.3 Hz, C$_9$H$_6$NCH=CHC$_6$H$_4$—),
8.12 (1H, d, J = 8.5 Hz, quinoline C5-H),
8.17–8.20 (1H, m, quinoline C8-H),
8.29 (1H, m, C5-H/C7-H),
8.31 (1H, m, C5-H/C7-H),
8.50 (1H, d, J = 8.6 Hz, quinoline C4-H),
8.57–8.58 (1H, br.s, C2'-H).

EXAMPLE 40

Synthesis of 8-carboxy-6-fluoro-3'-[2-(2-quinolinyl)ethenyl]flavone

In a similar manner as in Example 34, the title copound represented by the following formula was obtained from 3-[2-(2-quinolinyl) ethenyl]benzaldehyde and 3-carboxy-5-fluoro-2-hydroxyacetophenone (yield: 30%).

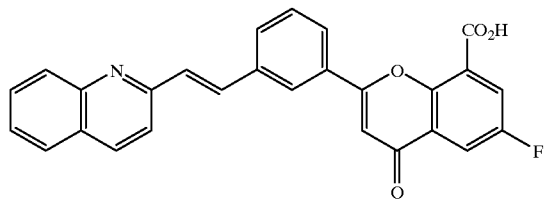

m.p.: >300° C.

$^1$H-NMR(DMSO-$d_6$) ; δ7.28 (1H, s, C3-H),
7.56–7.59 (1H, m, quinoline C6-H),
7.64 (1H, t, J = 7.8 Hz, C5'-H),
7.66 (1H, d, J = 16.4 Hz, olefin-H),
7.75–7.79 (1H, m, quinoline C7-H),
7.85 (1H, d, J = 8.5 Hz, quinoline C3-H),
7.89 (1H, d, J = 16.4 Hz, olefin-H),
7.94–7.97 (3H, m, C5-H/C7-H, C4'-H, quinoline C5-H),
8.02 (1H, d, J = 8.4 Hz, quinoline C8-H),
8.09 (1H, dd, J = 8.5 Hz, 3.2 Hz, C5-H/C7-H),
8.16 (1H, d, J = 7.8 Hz, C6'-H),
8.37 (1H, d, J = 8.5 Hz, quinoline C4-H),
8.57 (1H, br.s, C2'-H).

EXAMPLE 41

Synthesis of 8-carboxy-6-chloro-3'-[2-(2-quinolinyl)ethenyl]flavone

In a similar manner as in Example 34, the title compound represented by the following formula was ob- tained from 3-[2-(2-quinolinyl)ethenyl]benzaldehyde and 3-carboxy-5-chloro-2-hydroxyacetophenone (yield: 8%).

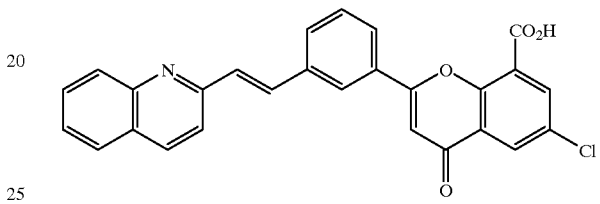

m.p.: >300° C.

$^1$H-NMR(DMSO-$d_6$) ; δ7.35 (1H, s, C3-H),
7.56-7.60 (1H, m, quinoline C6-H),
7.63 (1H, t, J = 7.8 Hz, C5'-H),
7.67 (1H, d, J = 16.3 Hz, C$_9$H$_6$NCH=CHC$_6$H$_4$—),
7.75–7.79 (1H, m, quinoline C7-H),
7.87 (1H, d, J = 8.5 Hz, quinoline C3-H),
7.89 (1H, d, J = 16.3 Hz, C$_9$H$_6$NCH=CHC$_6$H$_4$—),
7.94–7.97 (2H, m, C4'-H, quinoline C5-H),
8.00 (1H, d, J = 8.3 Hz, quinoline C8-H),
8.13 (1H, d, J = 2.7 Hz, C5-H/C7-H),
8.17 (1H, d, J = 7.9 Hz, C6'-H),
8.20 (1H, d, J = 2.7 Hz, C5-H/C7-H),
8.37 (1H, d, J = 8.5 Hz, quinoline C4-H),
8.61 (1H, s, C2'-H).

EXAMPLE 42

Synthesis of 8-carboxy-6-bromo-3'-[2-(2-quinolinyl)ethenyl]flavone

In a similar manner as in Example 34, the title compound represented by the following formula was obtained from 3-[2-(2-quinolinyl)ethenyl]benzaldehyde and 3-carboxy-5-bromo-2-hydroxyacetophenone (yield: 56%).

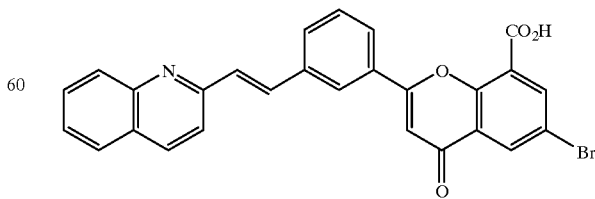

m.p.: >300° C.

¹H-NMR(DMSO-d₆) ; δ7.31 (1H, s, C3-H), 7.55–7.59 (1H, m, quinoline C6-H),
7.61–7.66 (1H, m, C5'-H),
7.65 (1H, d, J = 16. 0 Hz, C₉H₆NCH=CHC₆H₄—),
7.75–7.79 (1H, m, quinoline C7-H),
7.85 (1H, d, J = 8.6 Hz, quinoline C3-H),
7.88 (1H, d, J = 16.0 Hz, C₉H₆NCH=CHC₆H₄—),
7.93–7.96 (2H, m, C4'-H, quinoline C5-H),
8.01 (1H, d, J = 8.6 Hz, quinoline C8-H),
8.15 (1H, d, J = 7.8 Hz, C6'-H),
8.31 (1H, d, J = 2.6 Hz, C5-H/C7-H),
8.34 (1H, d, J = 2.6 Hz, C5-H/C7-H),
8.37 (1H, d, J = 8.6 Hz, quinoline C4-H),
8.57 (1H, s, C2'-H).

EXAMPLE 43

Synthesis of 8-carboxy-6-methyl-3'-[2-(2-quinolinyl)ethenyl]flavone

In a similar manner as in Example 34, the title compound represented by the following formula was obtained from 3-[2-(2-quinolinyl)ethenyl]bqnzaldehyde and 3-carboxy-5-methyl-2-hydroxyacetophenone (yield: 35%).

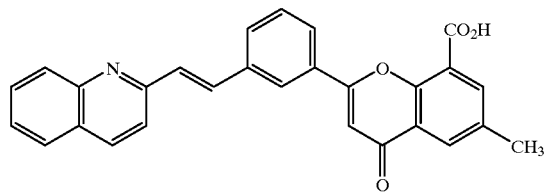

m.p.: >300° C.

¹H-NMR(DMSO-d₆) ; δ2.48 (3H, s, CH₃), 7.21 (1H, s, C3-H),
7.55–7.59 (1H, m, quinoline C6-H),
7.63 (1H, t, J = 7.5 Hz, C5'-H),
7.64 (1H, d, J = 15.6 Hz, olefin-H),
7.74–7.78 (1H, m, quinoline C7-H);
7.86 (1H, d, J = 8.5 Hz, quinoline C3-H),
7.89 (1H, d, J = 15.6 Hz, olefin-H),
7.92–7.96 (2H, m, C4'-H, quinoline C5-H),
8.02 (1H, d, J = 8.4 Hz, quinoline C8-H),
8.06 (1H, d, J = 2.2 Hz, C5-H/C7-H),
8.12 (1H, d, J = 2.2 Hz, C5-H/C7-H),
8.15 (1H, d, J = 8.2 Hz, C6'-H),
8.36 (1H, d, J = 8.5 Hz, quinoline C4-H),
8.56 (1H, s, C2'-H).

EXAMPLE 44

Synthesis of 6-chloro-8-cyano-3'-[2-(2-quinolinyl)ethenyl]flavone

In a similar manner as in Example 34, the title compound represented by the following formula was obtained from 3-[2-(2-quinolinyl)ethenyl]benzaldehyde and 5-chloro-3-cyano-2-hydroxyacetophenone (yield: 53%).

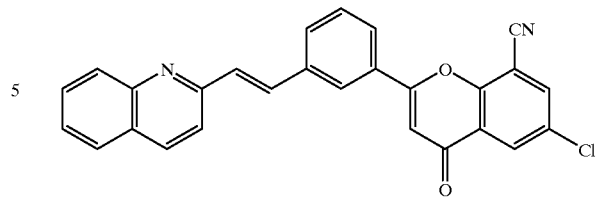

m.p.: 281.2–281.6° C.

¹H-NMR(DMSO-d₆) ; δ7.37 (1H, s, C3-H), 7.56–7.60 (1H, m, quinoline C6-H),
7.69 (1H, d, J = 16.5 Hz, olefin-H),
7.70–7.74 (1H, m, C5'-H),
7.75–7.79 (1H, m, quinoline C7-H),
7.85 (1H, d, J = 8.6 Hz, quinoline C3-H),
7.90–8.07 (5H, m, olefin-H, C4'-H, C6'-H, quinoline C5-H, quinoline C8-H),
8.27 (2H, d, J = 1.9 Hz, C5-H/C7-H),
8.38 (1H, d, J = 8.5 Hz, quinoline C4-H),
8.49 (1H, s, C2'-H),
8.54 (1H, d, J = 1.9 Hz, C5-H/C7-H).

Example 45

Synthesis of 6-chloro-3'-[2-(2-quinolinyl)ethenyl]-8-(5-tetrazolyl)flavone

In a similar manner as in Example 34, the title compound represented by the following formula was obtained from 3-[2-(2-quinolinyl)ethenyl]benzaldehyde and 5-chloro-2-hydroxy-3-(5-tetrazolyl)acetophenone (yield: 9%).

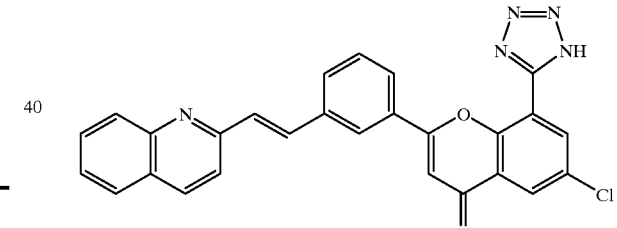

m.p.: >300° C.

¹H-NMR(DMSO-d₆) ; δ7.37 (1H, s, C3-H),
7.58–7.65 (3H, m, olefin-H, C5'-H, quinoline C6-H),
7.76–7.80 (1H, m, quinoline C7-H),
7.87 (1H, d, J = 8.0 Hz, quinoline C3-H),
7.92–8.05 (5H, m, olefin-H, C4'-H, C6'-H, quinoline C5-H, quinoline C8-H),
8.25 (1H, d, J = 2.4 Hz, C5-H),
8.41 (1H, s, C2'-H),
8.44 (1H, d, J = 2.3 Hz, C7-H),
8.47 (1H, d, J = 8.5 Hz, quinoline C4-H),
9.54 (1H, s, CN4H).

EXAMPLE 46

Synthesis of 6-carboxy-3-hydroxyflavone

5'-Carboxy-2'-hydroxychalcone (30 mmol) and sodium hydroxide (5.2 g, 130 mmol) were dissolved in 200 ml of ethanol, to which 11.4 ml (100 mmol) of a 30% aqueous solution of hydrogen peroxide were added under ice cooling. The reaction mixture was stirred at 0° C. for 2 hours and then at room temperature for 16 hours. 2 N hydrochloric acid was added to the reaction mixture to acidify the same. The resulting precipitate was collected by filtration, washed with water, dried in air, and then recrystallized from THF-EtOH, whereby the title compound represented by the following formula was obtained (yield: 83%).

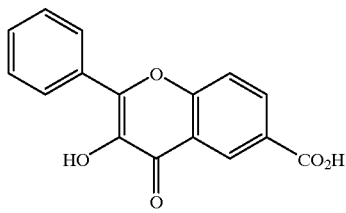

m.p.: >250° C.

$^1$H-NMR(DMSO-$d_6$); δ7.55 (3H, m, C3'-H, C4'-H, C5'-H),
7.85 (1H, d, J = 8.7 Hz, C8-H),
8.22 (2H, m, C2'-H, C6'-H),
8.28 (1H, dd, J = 8.7 Hz, C7-H),
8.65 (1H, d, J = 2.2 Hz, C5-H),
9.90 (1H, br.s, OH), 13.26 (1H, br.s, COOH).

EXAMPLE 47

Synthesis of 6-bromo-8-carboxy-3-hydroxyflavone

In a similar manner as in Example 46, the title compound represented by the following formula was obtained from 5'-bromo-3'-carboxy-2'-hydroxychalcone (yield: 56%).

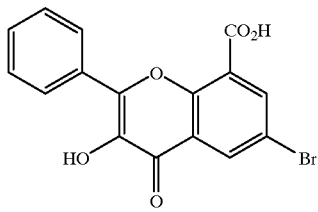

m.p.: >250° C.

$^1$H-NMR (DMSO-$d_6$); δ 7.54 (3H, m, C3'-H, C4'-H, C5'-H), 8.35 (4H, m, C5-H, C7-H, C6-H, C2-H), 10.10 (1H, br.s, OH), 13.86 (1H, br.s, COOH).

EXAMPLE 48

Synthesis of 6-carboxy-3',4'-dichloro-3-hydroxyflavone

In a similar manner as in Example 46, the title compound represented by the following formula was obtained from 3'-carboxy-3,4-dichloro-2'-hydroxychalcone (yield: 44%).

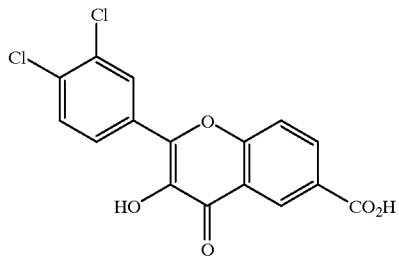

m.p.: >250° C.

| $^1$H-NMR (DMSO-$d_6$); | δ7.85 (2H, m, C8-H, C5'-H), |
|---|---|
| | 8.05 (1H, dd, J = 8.2 Hz, C6'-H), |
| | 8.27 (1H, d, J = 2.4 Hz, C2'-H), |
| | 8.40 (1H, dd, J = 2.2 Hz, 8.7 Hz, C7-H), |
| | 8.60 (1H, d, J = 2.2 Hz, C5-H), |
| | 10.35 (1H, br.s, OH), |
| | 13.20 (1H, br.s, COOH). |

EXAMPLE 49

Synthesis of 3-(3-chloropropoxy)-6-ethoxycarbonylflavone

1) Concentrated sulfuric acid (1 ml) was added to a solution of 6-carboxy-3-hydroxyflavone (10 mol) in 200 ml of ethanol, followed by refluxing for 24 hours. After the reaction mixture was allowed to cool down, an insoluble matter was removed, and the reaction mixture was concentrated at room temperature. The residue was dissolved in chloroform. The thus-obtained solution was washed with a saturated aqueous solution of sodium hydrogencarbonate and water, dried over anhydrous sodium sulfate, and then concentrated under reduced pressure. Without purification, 6-ethoxycarbonyl-3-hydroxyflavone obtained as described above was provided for use in the next reaction.

2) 6-Ethoxycarbonyl-3-hydroxyflavone (3.2 mmol), 1-bromo-3-chloropropane (3.2 mmol) and potassium carbonate (3.2 mmol) were dissolved in 20 ml of DMF, followed by stirring at 100° C. for 2 hours. The reaction mixture was concentrated under reduced pressure. Chloroform was added to the residue, and an insoluble mater was removed. The filtrate was concentrated under reduced pressure. The residue was purified by chromatography on a silica gel column (petroleum ether:ethyl acetate=2:1), whereby the title compound represented by the following formula was obtained as a colorless oil (yield: 38%).

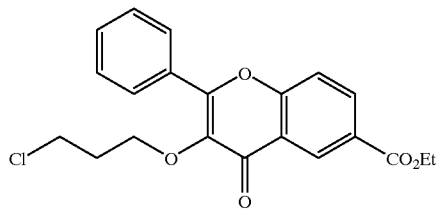

¹H-NMR(CDCl₃) ;   δ1.35 (3H, t, J = 7.1 Hz, OCH₂CH₃),
2.05 (2H, m, ClCH₂CH₂CH₂O),
3.65 (2H, t, J = 6.4 Hz, ClCH₂CH₂CH₂O),
4.15 (2H, t, J = 5.9 Hz, ClCH₂CH₂CH₂O),
4.35 (2H, q, J = 7.1 Hz, OCH₂CH₃),
7.45 (3H, m, C3'-H, C4'-H, C5'-H),
7.95 (3H, m, C8-H, C2'-H, C6'-H),
8.25 (1H, dd, J = 2.2 Hz, 8.7 Hz, C7-H),
8.80 (1H, d, J = 2.2 Hz, C5-H).

EXAMPLE 50

Synthesis of 6-bromo-3-(3-chloropropoxy)-8-ethoxycarbonylflavone

In a similar manner as in Example 49, the title compound represented by the following formula was obtained as a colorless oil from 6-bromo-8-carboxy-3-hydroxyflavone (yield: 35%).

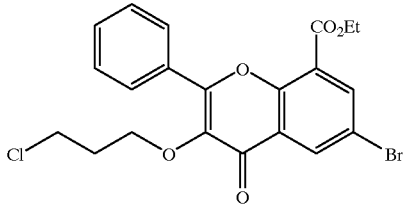

¹H-NMR(CDCl₃) ;   δ1.48 (3H, t, J = 7.1 Hz, OCH₂CH₃),
2.20 (2H, m, ClCH₂CH₂CH₂O),
3.70 (2H, t, J = 6.1 Hz, ClCH₂CH₂CH₂O),
4.25 (2H, t, J = 5.9 Hz, ClCH₂CH₂CH₂O),
4.50 (2H, q, J = 7.1 Hz, OCH₂CH₃),
7.58 (3H, m, C3'-H, C4'-H, C5'-H),
8.25 (2H, m, C2'-H, C6'-H),
8.40 (1H, d, J = 2.2 Hz, C7-H),
8.56 (1H, d, J = 2.2 Hz, C5-H).

EXAMPLE 51

Synthesis of 3-(3-chloropropoxy)-3',4'-dichloro-6-ethoxycarbonylflavone

In a similar manner as in Example 49, the title compound represented by the following formula was obtained as a pale yellow oil from 6-carboxy-3,4-dichloro-3-hydroxyflavone (yield: 45%).

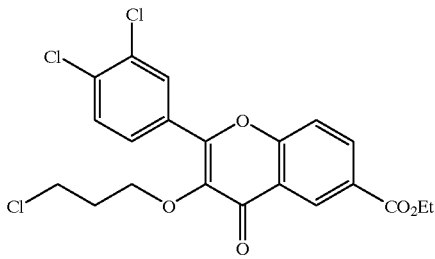

¹H-NMR(CDCl₃) ;   δ1.42 (3H, t, J = 7.1 Hz, OCH₂CH₃),
2.20 (2H, m, ClCH₂CH₂CH₂O),
3.70 (2H, t, J = 6.1 Hz, ClCH₂CH₂CH₂O),
4.25 (2H, t, J = 5.9 Hz, ClCH₂CH₂O),
4.45 (2H, q, J = 7.1 Hz, OCH₂CH₃),
7.60 (2H, m, C8-H, C5'-H),
8.00 (1H, dd, J = 2.4 Hz, 8.2 Hz, C6'-H),
8.15 (1H, d, J = 2.4 Hz, C2'-H),
8.90 (1H, d, J = 2.2 Hz, C5-H).

EXAMPLE 52

Synthesis of 6-ethoxycarbonyl-3-[3-(4-(2-quinolinylmethyl)piperazin-1-yl)propoxy]flavone 3-(3-Chloropropoxy)-6-ethoxycarbonylflavone (1.2 mmol), 1-(2-quinolinylmethyl)piperazine (0.32 g, 1.2 mmol), sodium hydrogencarbonate (0.31 g, 2.9 mmol) and sodium iodide (0.43 g, 2.9 mmol) were dissolved in 25 ml of 2-butanone, followed by overnight refluxing. The reaction mixture was concentrated under reduced pressure. Chloroform was added to the residue, and an insoluble matter was removed. The filtrate was concentrated under reduced pressure. The residue was purified by chromatography on a silica gel column (ethyl acetate:methanol=5:1), whereby the title compound represented by the following formula was obtained as a brown oil (yield: 75%).

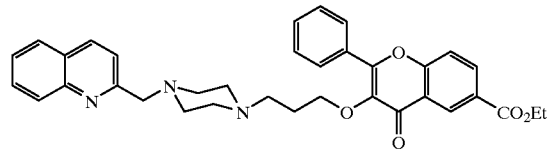

¹H-NMR (CDCl₃) ;   δ1.35 (3H, t, J= 7.1 Hz, OCH₂CH₃),
1.85 (2H, m, NCH₂CH₂CH₂O),
2.50 (10H, m, NCH₂CH₂CH₂O, piperazine),
3.78 (2H, s, C₉H₆NCH₂N),
4.05 (2H, t, J = 5.9 Hz, NCH₂CH₂CH₂O),
4.35 (2H, q, J = 7.1 Hz, OCH₂CH₃),
7.40–7.65 (8H, m, Ar-H), 8.00 (4H, m, Ar-H),
8.25 (1H, dd, J = 2.2 Hz, 8.7 Hz, C7-H),
8.88 (1H, d, J = 2.2 Hz, C5-H).

EXAMPLE 53

Synthesis of 6-bromo-8-ethoxycarbonyl-3-[3-(4-(2-quinolinylmethyl)piperazin-1-yl)propoxy]flavone In a similar manner as in Example 52, the title compound represented by the following formula was obtained as a brown oil from 6-bromo-3-(3-chloropropoxy)-8-ethoxycarbonylflavone (yield: 65%).

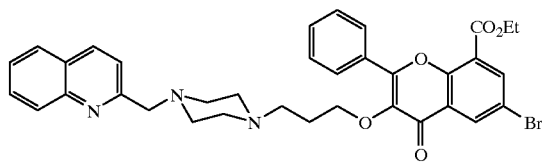

¹H-NMR(CDCl₃) ; δ1.37 (3H, t, J = 7.1 Hz, OCH₂CH₃),
1.85 (2H, m, NCH₂CH₂CH₂O),
2.01–2.57 (10H, m, NCH₂CH₂CH₂O, piperazine),
3.75 (2H, s, C₉H₆NCH₂N),
4.06 (2H, t, J = 5.9 Hz, NCH₂CH₂CH₂O),
4.40 (2H, q, J = 7.1 Hz, OCH₂CH₃),
7.38–7.73 (7H, m, Ar-H), 8.01 (2H, t, J = 8.1 Hz, Ar-H),
8.20 (2H, m, C2'-H, C6'-H),
8.27 (1H, dd, J = 2.2 Hz, 8.7 Hz, C7-H),
8.46 (1H, d, J = 2.2 Hz, C5-H)

EXAMPLE 54

Synthesis of 3',4'-dichloro-6-ethoxycarbonyl-3-[3-{4-(2-quinolinylmethyl)piperazin-1-yl}propoxy]flavone In a similar manner as in Example 52, the title compound represented by the following formula was obtained as a brown oil from 3-(3-chloropropoxy)-3',4'-dichloro-6-ethoxycarbonylflavone (yield: 72%).

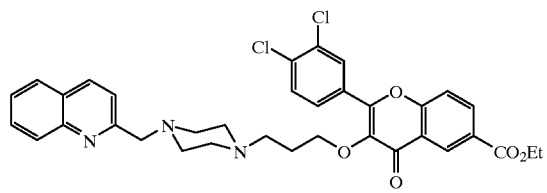

¹H-NMR(CDCl₃) ; δ1.35 (3H, t, J = 7.1 Hz, OCH₂CH3),
1.95 (2H, m, NCH₂CH₂CH₂O),
2.55 (10H, m, NCH₂CH₂CH₂O, piperazine);
3.80 (2H, s, C₉H₆NCH₂N),
4.10 (2H, t, J = 5.9 Hz, NCH₂CH₂CH₂O),
4.35 (2H, q, J = 7.1 Hz, OCH₂CH₃),
7.45–7.65 (6H, m, Ar-H),
7.90–8.15 (4H, m, Ar-H),
8.30 (1H, dd, J = 2.2 Hz, 7.8 Hz, C7-H),
8.85 (1H, d, J = 2.2 Hz, C5-H).

EXAMPLE 55

Synthesis of 6-carboxy-3-[3-{4-(2-quinolinylmethyl)piperazin-1-yl}propoxy]flavone 6-Ethoxycarbonyl-3-[3-{4-(2-quinolinylmethyl)piperazin-1-yl}propoxy]flavone (0.8 mmol) was dissolved in 20 ml of ethanol, followed by the addition of 2 ml of a saturated aqueous solution of sodium hydrogencarbonate. The reaction mixture was refluxed for 2 hours and was then allowed to cool down. The solvent was driven off under reduced pressure. Acetic acid was added to the residue to neutralize the same, followed by extraction with chloroform. After the organic layer was concentrated under reduced pressure, the residue was recrystallized from EtOH-ether, whereby the title compound represented by the following formula was obtained (yield: 74%).

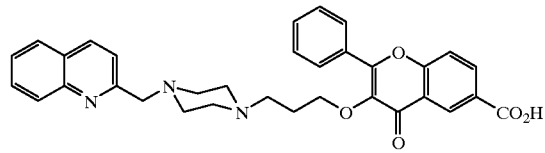

m.p.: 146–148° C.

¹H-NMR(CDCl₃) ; δ2.08 (2H, m, NCH₂CH₂CH₂O),
2.90 (10H, m, NCH₂CH₂CH₂O, piperazine),
3.85 (2H, s, C₉H₆NCH₂N),
4.05 (2H, t, J = 5.9 Hz, NCH₂CH₂CH₂O),
7.40–7.70 (8H, m, Ar-H), 7.95– 8.10 (4H, m, Ar-H),
8.25 (1H, dd, J = 2.2 Hz, 8.7 Hz, C7-H),
8.80 (1H, d, J = 2.2 Hz, C5-H), 10.95 (1H, br.s, COOH).

EXAMPLE 56

Synthesis of 6-bromo-8-carboxy-3-[3-{4-(2-quinolinylmethyl)piperazin-1-yl}propoxy]flavone In a similar manner as in Example 55, the title compound represented by the following formula was obtained from 6-bromo-8-ethoxycarbonyl-3-[3-{4-(2-quinolinylmethyl)piperazin-1-yl}propoxy]flavone (yield: 90%).

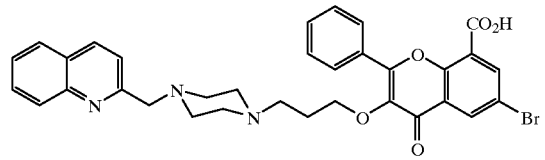

m.p.: 125–126° C.

¹H-NMR(CDCl₃) ; δ1.95 (2H, m, NCH₂CH₂CH₂O),
2.50–2.53 (10H, m, NCH₂CH₂CH₂O, piperazine),
3.83 (2H, s, C₉H₆NCH₂N),
4.08 (2H, t, J = 5.9 Hz, NCH₂CH₂CH₂O),
7.43–7.75 (7H, m, Ar-H), 7.95 (2H, t, J = 8.1 Hz, Ar-H),
8.13 (1H, d, J = 2.2 Hz, C7-H),
8.16 (2H, m, C2'-H, C6'-H), 8.35 (1H, d, J = 2.2 Hz, C5-H),
11.75 (1H, br.s, COOH).

EXAMPLE 57

Synthesis of 6-carboxy-3',4'-dichloro-3-[3-{4-(2-quinolinylmethyl)piperazin-1-yl}propoxy]flavone In a similar manner as in Example 55, the title compound represented by the following formula was obtained from 3',4'-dichloro-6-ethoxycarbonyl-3-[3-{4-(2-quinolinylmethyl)piperazin-1-yl}propoxy]flavone (yield: 82%).

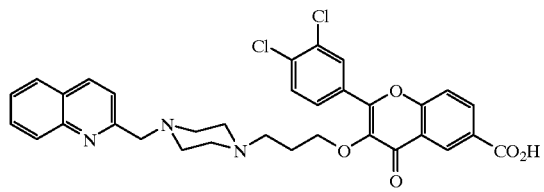

m.p.: 134–135° C.

$^1$H-NMR(CDCl$_3$) ; δ1.98 (2H, m, NCH$_2$CH$_2$CH$_2$O),
3.05 (10H, m, NCH$_2$CH$_2$CH$_2$O, piperazine),
3.90 (2H, s, C$_9$H$_5$NCH$_2$N),
4.10 (2H, t, J = 5.9 Hz, NCH$_2$CH$_2$CH$_2$O),
7.55–7.75 (6H, m, Ar-H), 8.00 (4H, m, Ar-H),
8.30 (1H, dd, J = 2.2 Hz, 8.7 Hz, C7-H),
8.88 (1H, d, J = 2.2 Hz, C5-H), 11.70 (1H, br.s, COOH).

TEST 1

Antileucotriene D$_4$ Action (In Vitro Test)

An isolated guinea pig ileum was cut into about 2 cm lengths. Each ileum piece was suspended in a 20-ml container filled with the Krebs buffer. An isotonic constractive response by leukotriene D$_4$ was recorded on a recorder. The Krebs buffer was controlled at 37° C., through which a mixed gas (95%O$_2$–5%CO$_2$) was bubbled. First, leukotriene D$_4$ was added to an organ bath to measure its dose-response. After the ileum piece was washed several times with the buffer, a test compound (will be identified by its example number; this will apply likewise hereinafter) of a predetermined specific concentration was added. Subsequent to incubation for 30 minutes, the dose-response of leukotriene D$_4$ was measured. The results are shown in Table 1.

TABLE 1

| Test comp'd | Anti-LT action (IC$_{50}$) |
|---|---|
| 23 | 6.1 × 10$^{-8}$ M |
| 41 | 1.5 × 10$^{-8}$ M |
| 42 | 1.0 × 10$^{-7}$ M |
| 43 | 2.8 × 10$^{-8}$ M |

TEST 2

Leukotriene D$_4$ Receptor Binding Inhibition Test

Incubated for 30 minutes was 0.3 ml of a 10 mM piperazine N,N'-bis(2-ethanesulfonate) buffer (pH 7.5) which contained 0.2 nM [$^3$H]leukotriene D$_4$, guinea pig pulmomembranous protein and a test compound. An ice-cooled tris hydrochloride/sodium chloride buffer (10 mM/100 mM, pH 7.5) was added to terminate the reaction, followed by immediate filtration through a Wattman CF/C filter. The filter was washed twice with 20 ml aliquots of the ice-cooled buffer. The radioactivity of the residue was measured by a liquid scintillation counter. From a measurement value obtained without the addition of the test compound and measurements values obtained upon addition of the test compound at various concentrations, the dose-response of the inhibitory action of the test compound was measured and the 50% inhibitory concentration (IC$_{50}$) was determined. Using the Cheng-Prusoff formula, a dissociation constant (K$_D$) was calculated from the IC$_{50}$. From a binding assay, it was found that the maximum binding (Bmax) of 2 μM leucotriene D$_4$ was 988 fmol/mg protein. Further, the dissociation constant (K$_D$) of [$^3$H]leukotriene D$_4$ was 2.16×10$^{-10}$M and when analyzed by a Hill plot, its slope was found to be 0.99. Incidentally, the values in Table 2 indicate dissociation constants K$_D$ (mol).

TABLE 2

| Test comp'd | LTD receptor (%) |
|---|---|
| 5 | 5.04 × 10$^{-7}$ M |
| 14 | 1.11 × 10$^{-8}$ M |
| 17 | 2.10 × 10$^{-7}$ M |
| 18 | 7.94 × 10$^{-8}$ M |
| 19 | 5.26 × 10$^{-7}$ M |
| 21 | 1.10 × 10$^{-6}$ M |
| 22 | 1.68 × 10$^{-8}$ M |
| 23 | 3.13 × 10$^{-8}$ M |
| 24 | 1.11 × 10$^{-8}$ M |
| 25 | 1.01 × 10$^{-7}$ M |
| 26 | 1.13 × 10$^{-6}$ M |
| 27 | 7.94 × 10$^{-8}$ M |
| 28 | 2.10 × 10$^{-7}$ M |
| 29 | 8.05 × 10$^{-7}$ M |
| 31 | 9.16 × 10$^{-6}$ M |
| 32 | 4.02 × 10$^{-6}$ M |
| 33 | 3.82 × 10$^{-7}$ M |
| 35 | 4.08 × 10$^{-7}$ M |
| 36 | 1.75 × 10$^{-6}$ M |
| 37 | 3.07 × 10$^{-7}$ M |
| 38 | 2.70 × 10$^{-7}$ M |
| 39 | 1.73 × 10$^{-8}$ M |
| 40 | 1.27 × 10$^{-7}$ M |
| 41 | 1.08 × 10$^{-8}$ M |
| 42 | 1.65 × 10$^{-8}$ M |
| 43 | 1.26 × 10$^{-8}$ M |
| 45 | 1.10 × 10$^{-8}$ M |

From the results of Table 1 and Table 2, the compounds (1) according to the present invention have excellent cyc-Lt$_1$ receptor antagonism and antileucotriene action.

The flavone derivatives (1) and their salts and solvates, according to the present invention, have excellent cyc-LT$_1$ receptor antagonism, and are therefore useful as medicine for the prevention or therapy of various allergic diseases and inflammatory diseases such as asthma, allergic rhinitis, allergic dermatitis, allergic conjunctivitis, urticaria, psoriasis, rheumatism, inflammatory colitis, cerebral ischemia or cerebral apoplexy.

What is claimed is:

1. A flavone derivative represented by the following formula (1):

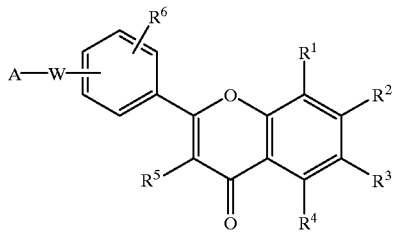
(1)

wherein A represents a hydrogen atom, a halogen atom, a substituted or unsubstituted phenyl group, a substituted or unsubstituted naphthyl group, or a group represented by the following formula (2):

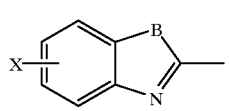
(2)

wherein X represents a hydrogen atom or a halogen atom, and B represents —CH=CH—, —CH—N—, —N($R^7$)— in which $R^7$ represents a lower alkyl group or an alkoxyalkyl group, —O— or —S—, W represents a single bond, —CH$_2$O— or —CH=CH—, at least one of $R^1$, $R^2$, $R^3$ and $R^4$ represents a carboxyl group, a cyano group, a substituted or unsubstituted alkyloxycarbonyl group, a tetrazolyl group, or —CONHR$^8$ in which $R^8$ represents a hydrogen atom, a lower alkyl group or a phenylsulfonyl group, and the remainder thereof may be the same or different and individually represent a hydrogen atom, a halogen atom, a hydroxyl group, a lower alkyl group or a lower alkoxyl group, $R^5$ represents a hydrogen atom, a hydroxyl group, a substituted or unsubstituted lower alkoxyl group, —O(CH$_2$)$_m$NR$^9$R$^{10}$ in which $R^9$ and $R^{10}$ may be the same or different and individually represent a hydrogen atom or a lower alkyl group or are coupled together with the adjacent nitrogen atom to form a phthalimido group, and m stands for a number of 1–5, or a group represented by the following formula (3):

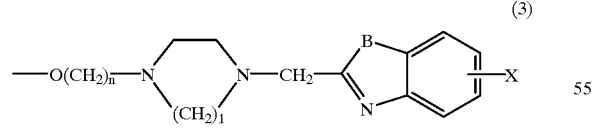
(3)

wherein n stands for a number of 1–5, l stands for a number of 2–3, and B and X have the same meanings as defined above, and $R^6$ represents a hydrogen atom, a halogen atom, a lower alkyl group or a lower alkoxyl group, with the proviso that a situation where A is a hydrogen atom or a halogen atom, W is a single bond and $R^5$ is a hydrogen atom is excluded; or a salt of said flavone derivative.

2. The compound of claim 1, wherein in the formula (1),

A represents a substituted or unsubstituted phenyl group, a substituted or unsubstituted naphthyl group, or a group represented by the following formula (2):

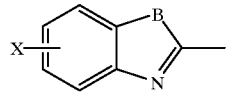
(2)

wherein X represents a hydrogen atom or a halogen atom, and B represents —CH=CH—, —CH—N—, —N($R^7$)— in which $R^7$ represents a lower alkyl group or an alkoxyalkyl group, —O— or —S—, W represents —CH$_2$O— or —CH=CH—, at least one of $R^1$, $R^2$, $R^3$ and $R^4$ represents a carboxyl group, a cyano group, a substituted or unsubstituted alkyloxycarbonyl group, a tetrazolyl group, or —CONHR$^8$ in which $R^8$ represents a hydrogen atom, a lower alkyl group or a phenylsulfonyl group, and the remainder thereof may be the same or different and individually represent a hydrogen atom, a halogen atom, a hydroxyl group, a lower alkyl group or a lower alkoxyl group, $R^5$ represents a hydrogen atom, a hydroxyl group, a substituted or unsubstituted lower alkoxyl group, —O(CH$_2$)$_m$NR$^9$R$^{10}$ in which $R^9$ and $R^{10}$ may be the same or different and individually represent a hydrogen atom or a lower alkyl group or are coupled together with the adjacent nitrogen atom to form a phthalimido group, and m stands for a number of 1–5, or a group represented by the following formula (3):

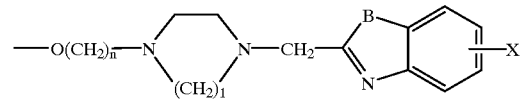
(3)

wherein n stands for a number of 1–5, l stands for a number of 2–3, and B and X have the same meanings as defined above, and $R^6$ represents a hydrogen atom, a halogen atom, a lower alkyl group or a lower alkoxyl group.

3. The compound of claim 1, wherein in the formula (1),

A represents a substituted or unsubstituted phenyl group, a substituted or unsubstituted naphthyl group, or a group represented by the following formula (2):

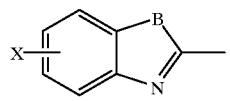
(2)

wherein X represents a hydrogen atom or a halogen atom, and B represents —CH=CH—, —CH—N—, —N($R^7$)— in which $R^7$ represents a lower alkyl group or an alkoxyalkyl group, —O— or —S—, W represents —CH$_2$O— or —CH=CH—, at least one of $R^1$, $R^2$, $R^3$ and $R^4$ represents a carboxyl group, a cyano group, a substituted or unsubstituted alkyloxycarbonyl group, a tetrazolyl group, or —CONHR$^8$ in which R$^8$ represents a hydrogen atom, a lower alkyl group or a phenylsulfonyl group, and the remainder thereof may be the same or different and individually represent a hydrogen atom, a halogen atom, a hydroxyl group, a lower alkyl group or a lower alkoxyl group, R$^5$ represents a hydrogen atom, a hydroxyl group, a substituted or unsubstituted lower alkoxyl group, or —O(CH$_2$)$_m$NR$^9$R$^{10}$ in which R$^9$ and R$^{10}$ may be the same or different and individually represent a hydrogen atom or a lower alkyl group or are coupled together with the adjacent nitrogen atom to form a phthalimido group, and m stands for a number of 1–5, and R$^6$ represents a hydrogen atom, a halogen atom, a lower alkyl group or a lower alkoxyl group.

4. The compound of claim 1, wherein in the formula (1),

A represents a hydrogen atom or a halogen atom,

W represents a single bond, at least one of R$^1$, R$^2$, R$^3$ and R$^4$ represents a carboxyl group, a cyano group, a substituted or unsubstituted alkyloxycarbonyl group, a tetrazolyl group, or —CONHR$^8$ in which R$^8$ represents a hydrogen atom, a lower alkyl group or a phenylsulfonyl group, and the remainder thereof may be the same or different and individually represent a hydrogen atom, a halogen atom, a hydroxyl group, a lower alkyl group or a lower alkoxyl group, R$^5$ represents a hydroxyl group, a substituted or unsubstituted lower alkoxyl group, —O(CH$_2$)$_m$NR$^9$R$^{10}$ in which R$^9$ and R$^{10}$ may be the same or different and individually represent a hydrogen atom or a lower alkyl group or are coupled together with the adjacent nitrogen atom to form a phthalimido group, and m stands for a number of 1–5, or a group represented by the following formula (3):

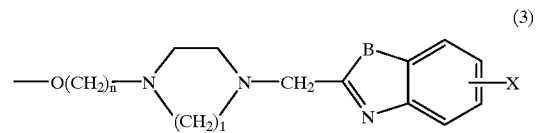

wherein n stands for a number of 1–5, l stands for a number of 2–3, and B and X have the same meanings as defined above, and R$^6$ represents a hydrogen atom, a halogen atom, a lower alkyl group or a lower alkoxyl group.

5. A medicine comprising as an effective ingredient the compound of any one of claims 1–4.

6. The medicine of claim 5, which is a cys-LT$_1$ receptor antagonist.

7. The medicine of claim 5, which is a preventive or therapeutic for an allergic disease.

8. The medicine of claim 5, which is a preventive or therapeutic for a disease selected from asthma, allergic rhinitis, allergic dermatitis, allergic conjunctivitis, urticaria, psoriasis, rheumatism, inflammatory colitis, cerebral ischemia or cerebral apoplexy.

9. A medicinal composition comprising the compound of any one of claims 1–4 and a pharmacologically acceptable carrier.

10. A treatment method of an allergic disease, which comprises administering an effective amount of the compound of claim 1.

11. The treatment method of claim 10, wherein said allergic disease is a disease selected from asthma, allergic rhinitis, allergic dermatitis, allergic conjunctivitis, urticaria, psoriasis, rheumatism, inflammatory colitis, cerebral ischemia or cerebral apoplexy.

\* \* \* \* \*